US010596222B2

(12) United States Patent
Kirk et al.

(10) Patent No.: US 10,596,222 B2
(45) Date of Patent: Mar. 24, 2020

(54) COMBINATION THERAPY WITH PEPTIDE EPOXYKETONES

(71) Applicant: Onyx Therapeutics, Inc., Thousand Oaks, CA (US)

(72) Inventors: Christopher J. Kirk, San Francisco, CA (US); Susan D. Demo, San Francisco, CA (US); Mark K. Bennett, Moraga Town, CA (US)

(73) Assignee: ONYX THERAPEUTICS, INC., Thousand Oaks, CA (US)

( * ) Notice: Subject to any disclaimer, the term of this patent is extended or adjusted under 35 U.S.C. 154(b) by 0 days.

(21) Appl. No.: 15/341,659

(22) Filed: Nov. 2, 2016

(65) Prior Publication Data

US 2017/0151305 A1 Jun. 1, 2017

Related U.S. Application Data

(60) Continuation of application No. 14/470,224, filed on Aug. 27, 2014, now Pat. No. 9,511,109, which is a division of application No. 13/125,292, filed as application No. PCT/US2009/061498 on Oct. 21, 2009, now abandoned.

(60) Provisional application No. 61/196,945, filed on Oct. 21, 2008.

(51) Int. Cl.
| *A61K 38/07* | (2006.01) |
| *A61K 31/165* | (2006.01) |
| *A61K 31/167* | (2006.01) |
| *A61K 45/06* | (2006.01) |
| *A61K 31/573* | (2006.01) |
| *A61K 31/335* | (2006.01) |
| *A61K 31/45* | (2006.01) |
| *A61K 31/198* | (2006.01) |
| *A61K 31/337* | (2006.01) |
| *A61K 31/704* | (2006.01) |
| *A61K 31/454* | (2006.01) |

(52) U.S. Cl.
CPC ............ *A61K 38/07* (2013.01); *A61K 31/165* (2013.01); *A61K 31/167* (2013.01); *A61K 31/198* (2013.01); *A61K 31/335* (2013.01); *A61K 31/337* (2013.01); *A61K 31/45* (2013.01); *A61K 31/454* (2013.01); *A61K 31/573* (2013.01); *A61K 31/704* (2013.01); *A61K 45/06* (2013.01)

(58) Field of Classification Search
None
See application file for complete search history.

(56) References Cited

U.S. PATENT DOCUMENTS

| 4,733,665 A | 3/1988 | Palmaz |
| 4,990,448 A | 2/1991 | Konishi et al. |
| 5,071,957 A | 12/1991 | Konishi et al. |
| 5,134,127 A | 7/1992 | Stella et al. |
| 5,135,919 A | 8/1992 | Folkman et al. |
| 5,340,736 A | 8/1994 | Goldberg |
| 5,376,645 A | 12/1994 | Stella et al. |
| 5,441,944 A | 8/1995 | Weisz et al. |
| 5,723,492 A | 3/1998 | Chandrakumar et al. |
| 5,756,764 A | 5/1998 | Fenteany et al. |
| 5,831,081 A | 11/1998 | Reuscher |
| 5,874,418 A | 2/1999 | Stella et al. |
| 6,046,177 A | 4/2000 | Stella et al. |
| 6,066,730 A | 5/2000 | Adams et al. |
| 6,075,150 A | 6/2000 | Wang et al. |
| 6,099,851 A | 8/2000 | Weisman et al. |
| 6,133,248 A | 10/2000 | Stella |
| 6,133,308 A | 10/2000 | Soucy et al. |
| 6,150,415 A | 11/2000 | Hammock et al. |
| 6,153,746 A | 11/2000 | Shah et al. |
| 6,204,257 B1 | 3/2001 | Stella et al. |
| 6,235,717 B1 | 5/2001 | Leban et al. |
| 6,294,560 B1 | 9/2001 | Soucy et al. |
| 6,297,217 B1 | 10/2001 | Adams et al. |
| 6,410,512 B1 | 6/2002 | Mundy et al. |
| 6,462,019 B1 | 10/2002 | Mundy et al. |
| 6,492,333 B1 | 12/2002 | Mundy |
| 6,548,668 B2 | 4/2003 | Adams et al. |
| 6,613,541 B1 | 9/2003 | Vaddi et al. |
| 6,617,309 B2 | 9/2003 | Tung et al. |
| 6,632,803 B1 | 10/2003 | Harding |
| 6,656,904 B2 | 12/2003 | Mundy et al. |

(Continued)

FOREIGN PATENT DOCUMENTS

| EP | 0 411 660 A1 | 2/1991 |
| EP | 1 136 498 A1 | 9/2001 |

(Continued)

OTHER PUBLICATIONS

Sharma et al. ("Melphalan and dexamethasone for patients with multiple myeloma who are not candidates for autologous stem cell transplantation" Natl. Med J. India May-Jun. 2007; 20(3):121-4).*
Kuhn et al. ("Potent activity of carfilzomib, an novel, irreversible inhibitor of the ubiquitin-proteasome pathway against preclinical models of multiple myeloma" Blood; 2007 110:3281-3290.*
Dimopoulos et al. ("Lenalidomide plus Dexamethasone for Relapsed or Refractory Multiple Myeloma", New England Journal of Medicine 2007;357:2123-32.*

(Continued)

*Primary Examiner* — James H Alstrum-Acevedo
*Assistant Examiner* — Tara L Martinez
(74) *Attorney, Agent, or Firm* — Marshall, Gerstein & Borun LLP

(57) ABSTRACT

The invention provides combination therapy, wherein one or more other therapeutic agents are administered agents are administered with peptide epoxyketones or a pharmaceutically acceptable salt thereof. Another aspect of the invention relates to treating cancer with a peptide epoxyketone administered in combination with another therapeutic agent.

6 Claims, 12 Drawing Sheets

(56) References Cited

U.S. PATENT DOCUMENTS

| | | |
|---|---|---|
| 6,660,268 B1 | 12/2003 | Palombella et al. |
| 6,699,835 B2 | 3/2004 | Plamondon et al. |
| 6,740,674 B2 | 5/2004 | Klimko et al. |
| 6,781,000 B1 | 8/2004 | Wang et al. |
| 6,794,516 B2 | 9/2004 | Soucy et al. |
| 6,831,099 B1 | 12/2004 | Crews et al. |
| 6,838,252 B2 | 1/2005 | Mundy et al. |
| 6,838,436 B1 | 1/2005 | Mundy et al. |
| 6,849,743 B2 | 2/2005 | Soucy et al. |
| 6,884,769 B1 | 4/2005 | Mundy et al. |
| 6,902,721 B1 | 6/2005 | Mundy et al. |
| 7,109,323 B2 | 9/2006 | Plamondon et al. |
| 7,189,740 B2 | 3/2007 | Zeldis |
| 7,232,818 B2 | 6/2007 | Smyth et al. |
| 7,388,017 B2 | 6/2008 | Tung et al. |
| 7,417,042 B2 | 8/2008 | Smyth et al. |
| 7,442,830 B1 | 10/2008 | Olhava et al. |
| 7,491,704 B2 | 2/2009 | Smyth et al. |
| 7,531,526 B2 | 5/2009 | Adams et al. |
| 7,635,773 B2 | 12/2009 | Antle |
| 7,687,456 B2 | 3/2010 | Zhou et al. |
| 7,691,852 B2 | 4/2010 | Shenk et al. |
| 7,700,588 B2 | 4/2010 | Merkus |
| 7,737,112 B2 | 6/2010 | Lewis et al. |
| 7,863,297 B2 | 1/2011 | Zeldis |
| 7,968,569 B2 | 6/2011 | Zeldis |
| 8,080,545 B2 | 12/2011 | Shenk et al. |
| 8,080,576 B2 | 12/2011 | Shenk et al. |
| 8,088,741 B2 | 1/2012 | Smyth et al. |
| 8,129,346 B2 | 3/2012 | Smyth et al. |
| 8,198,262 B2 | 6/2012 | Zeldis |
| 8,198,270 B2 | 6/2012 | Smyth et al. |
| 8,198,306 B2 | 6/2012 | Zeldis |
| 8,207,124 B2 | 6/2012 | Smyth et al. |
| 8,207,125 B2 | 6/2012 | Smyth et al. |
| 8,207,126 B2 | 6/2012 | Smyth et al. |
| 8,207,127 B2 | 6/2012 | Smyth et al. |
| 8,207,297 B2 | 6/2012 | Smyth et al. |
| 8,324,174 B2 | 12/2012 | Smyth et al. |
| 8,357,683 B2 | 1/2013 | Shenk et al. |
| 8,367,617 B2 | 2/2013 | Phiasivongsa et al. |
| 8,431,571 B2 | 4/2013 | Shenk et al. |
| 9,493,582 B2 | 11/2016 | Antle et al. |
| 9,511,109 B2 | 12/2016 | Kirk et al. |
| 2002/0103127 A1 | 8/2002 | Mundy et al. |
| 2002/0107203 A1 | 8/2002 | Mundy et al. |
| 2002/0111292 A1 | 8/2002 | Mundy et al. |
| 2003/0224469 A1 | 12/2003 | Buchholz et al. |
| 2003/0236223 A1 | 12/2003 | Wagner et al. |
| 2004/0097420 A1 | 5/2004 | Palombella et al. |
| 2004/0106539 A1 | 6/2004 | Schubert et al. |
| 2004/0116329 A1 | 6/2004 | Epstein |
| 2004/0138153 A1 | 7/2004 | Ramesh et al. |
| 2004/0167139 A1 | 8/2004 | Potter |
| 2004/0171556 A1 | 9/2004 | Purandare et al. |
| 2004/0254118 A1 | 12/2004 | He et al. |
| 2004/0266664 A1 | 12/2004 | Crews et al. |
| 2005/0025734 A1 | 2/2005 | Garrett et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis et al. |
| 2006/0241056 A1 | 10/2006 | Orlowski et al. |
| 2007/0105786 A1 | 5/2007 | Zhou et al. |
| 2007/0207950 A1 | 9/2007 | Yao et al. |
| 2007/0212756 A1 | 9/2007 | Greene et al. |
| 2008/0090785 A1 | 4/2008 | Smyth et al. |
| 2009/0099132 A1 | 4/2009 | Olhava et al. |
| 2009/0105156 A1 | 4/2009 | Phiasivongsa et al. |
| 2009/0131421 A1 | 5/2009 | Smyth et al. |
| 2009/0156473 A1 | 6/2009 | Schubert |
| 2009/0182149 A1 | 7/2009 | Kawahara et al. |
| 2009/0203698 A1 | 8/2009 | Zhou et al. |
| 2009/0215093 A1 | 8/2009 | Bennett et al. |
| 2010/0144648 A1 | 6/2010 | Shenk et al. |
| 2010/0240903 A1 | 9/2010 | Phiasivongsa et al. |
| 2011/0236428 A1 | 9/2011 | Kirk et al. |
| 2012/0077855 A1 | 3/2012 | Phiasivongsa et al. |
| 2012/0088762 A1 | 4/2012 | Shenk et al. |
| 2012/0088903 A1 | 4/2012 | Phiasivongsa et al. |
| 2012/0101025 A1 | 4/2012 | Smyth et al. |
| 2012/0101026 A1 | 4/2012 | Smyth et al. |
| 2012/0277146 A1 | 11/2012 | Smyth et al. |
| 2012/0329705 A1 | 12/2012 | Smyth et al. |
| 2013/0035295 A1 | 2/2013 | Kirk et al. |
| 2013/0041008 A1 | 2/2013 | Shenk et al. |
| 2013/0053303 A1 | 2/2013 | Shenk et al. |
| 2013/0065827 A1 | 3/2013 | Phiasivongsa |
| 2013/0072422 A1 | 3/2013 | Shenk et al. |
| 2013/0130968 A1 | 5/2013 | Zhou et al. |
| 2013/0150289 A1 | 6/2013 | Phiasivongsa et al. |
| 2013/0150290 A1 | 6/2013 | Phiasivongsa et al. |

FOREIGN PATENT DOCUMENTS

| | | |
|---|---|---|
| WO | WO-91/13904 A1 | 9/1991 |
| WO | WO-1994/15956 A1 | 7/1994 |
| WO | WO-1995/23797 A1 | 9/1995 |
| WO | WO-1995/24914 A1 | 9/1995 |
| WO | WO-1996/13266 A1 | 5/1996 |
| WO | WO-1996/32105 A1 | 10/1996 |
| WO | WO-1998/010779 A1 | 3/1998 |
| WO | WO-2000/002548 A2 | 1/2000 |
| WO | WO-2000/061167 A2 | 10/2000 |
| WO | WO-2001/028579 A2 | 4/2001 |
| WO | WO-02/30455 A2 | 4/2002 |
| WO | WO-2003/059898 A2 | 7/2003 |
| WO | WO-2004/089341 A1 | 10/2004 |
| WO | WO-2005/065649 A1 | 7/2005 |
| WO | WO-2005/105827 A2 | 11/2005 |
| WO | WO-2005/111008 A2 | 11/2005 |
| WO | WO-2005/111009 A2 | 11/2005 |
| WO | WO-2006/017842 A1 | 2/2006 |
| WO | WO-2006/045066 A2 | 4/2006 |
| WO | WO-2006/063154 A1 | 6/2006 |
| WO | WO-2006/086600 A1 | 8/2006 |
| WO | WO-2006/099261 A2 | 9/2006 |
| WO | WO-2006/113470 A2 | 10/2006 |
| WO | WO-2007/021666 A2 | 2/2007 |
| WO | WO-2007/056464 A1 | 5/2007 |
| WO | WO-2007/067976 A2 | 6/2007 |
| WO | WO-2007/138116 A2 | 12/2007 |
| WO | WO-2007/149512 A2 | 12/2007 |
| WO | WO-2008/033807 A2 | 3/2008 |
| WO | WO-2008/091620 A2 | 7/2008 |
| WO | WO-2008/122038 A1 | 10/2008 |
| WO | WO-2008/140782 A2 | 11/2008 |
| WO | WO-2009/020448 A1 | 2/2009 |
| WO | WO-2009/045497 A1 | 4/2009 |
| WO | WO-2009/051581 A1 | 4/2009 |
| WO | WO-2009/067453 A1 | 5/2009 |
| WO | WO-2009/154737 A1 | 12/2009 |
| WO | WO-2010/036357 A1 | 4/2010 |
| WO | WO-2010/048298 A1 | 4/2010 |
| WO | WO-2010/108172 A1 | 9/2010 |
| WO | WO-2010/145376 A1 | 12/2010 |
| WO | WO-2011/060179 A1 | 5/2011 |
| WO | WO-2011/109355 A1 | 9/2011 |
| WO | WO-2011/123502 A1 | 10/2011 |
| WO | WO-2011/136905 A2 | 11/2011 |
| WO | WO-2013/130666 A1 | 9/2013 |

OTHER PUBLICATIONS

Challa et al. (Cyclodextrins in Drug Delivery: An updated review; AAPS PharmSciTech; Oct. 14, 2005).*

Clinicaltrials.gov, Phase 1b Multicenter Study of Carfilzomib with Lenalidomide and Dexamethasone in Relapsed Multiple Myeloma, Apr. 4, 2008.

(56) References Cited

OTHER PUBLICATIONS

Proteolix Press Release, "Proteolix Initiates Phase 1b Clinical Trial of Carfilzomib in a Combination Regimen for Patients with Relapsed Multiple Myeloma", Jul. 10, 2008.
Richardson et al., Frequency, characteristics, and reversibility of peripheral neuropathy during treatment of advanced multiple myeloma with bortezomib, *J. Clin, Oncology*, 24(3):1-3 (2006).
Richardson et al., Phase 1/2 Study of Upfront Rev/Vel/Dex in MM: Early Results, *Haematologica*, 96(2), Supp. 2. PO-715 (Jun. 2007).
Smith et al., Bortezomib (Velcade TM) in the treatment of multiple myeloma, *Therapeutics & Risk Management*, 2(3):271-279 (2006).
"Definition of Cancer," [Retrieved from] http://www.medterms.com, 1 page [retrieved on Sep. 16, 2005].
Acharyya et al., "Cancer cachexia is regulated by selective targeting of skeletal muscle gene products" *J. Clin. Invest.* 114: 370-378 (2004).
Adams et al., "Proteasome Inhibitors: A Novel Class of Potent and Effective Antitumor Agents," *Cancer Res.* 59: 2615-22 (1999).
Adams, "The development of proteasome inhibitors as anticancer drugs," *Cancer Cell*, May 2003, 5:417-421.
Adams, Cancer Drug Discovery and Development. Protease Inhibitors in Cancer Therapy, 2004, Human Press, Chapter 20, Phase I trials, pp. 271-282.
Almond et al. "The proteasome: a novel target for cancer chemotherapy" *Leukemia*, 16(4), 433-443, Apr. 2002.
Altun et al., "Effects of PS-341 on the Activity and Composition of Proteasomes in Multiple Myeloma Cells" *Cancer Res* 65:7896, 2005.
Alves et al. "Diels-alder reactions of alkyl 2H-azirine-3-carboxylates with furans", *J. Chem. Soc. Perkin Trans*, 1:2969-2976, 2001.
Arastu Kapur et al., "Nonproteasomal targets of the proteasome inhibitors bortezomib and link to clinical adverse events," *Clin Cancer Res.*, 17:2734-43, 2011.
Argiriadi, "Binding of alkylurea inhibitors to epoxide hydrolase implicates active site tyrosines in substrate activation," *J. Biol. Chem.*, 2000, 275(20):15265-15270.
Bao et al. "PR-39 and PR-11 peptides inhibit ischemia-reperfusion injury by blocking proteasome-mediated IKBa degradation" *Am. J. Physiol. Heart Circ. Physiol.* 281:H2612-H2618, 2001.
Benedetti et al., Versatile and stereoselective synthesis of diamino diol dipeptide isosteres, core units of pseudopeptide HIV protease inhibitors, *J. Org. Chem.*, 1997, 62:9348-53.
Berge et al. "Pharmaceutical Salts", *J. Pharm. Sci.* 66(1), 1-19. Jan. 1977.
Bernier et al. "A Methionine aminopeptidase-2 Inhibitor, PPI-2458, for the treatment of rheumatoid arthritis", *Proc. Natl. Acad. Sci. USA*, 101(29):10768-73, Jul. 20, 2004.
Bis et al. "Defining & Addressing Solid-State Risks After the Proof-of-Concept Stage of Pharmaceutical Development," *Drug Development & Delivery*, pp. 32-34, 2011.
Blackburn et al., "Characterization of a new series of non-covalent proteasome inhibitors with exquisite potency and selectivity for the 20S PS-subunit," *Biochem J.*, 2010, 430:461-476.
Boccadoro et al. "Preclinical evaluation of the proteasome inhibitor bortezomib in cancer therapy", *Cancer Cell International*, 5(18), Jun. 1, 2005.
Bogyo et al. "Biochemistry", *Proc. Natl. Acad. Sci. USA*, 94:6629-6634, 1997.
Bogyo et al. "Substrate binding and sequence preference of the proteasome revealed by active-site-directed affinity probes", *Chemistry & Biology*, 5(6)307-320, Jun. 1998.
Bougauchi et al., "Catalytic Asymmetric Epoxidation of .alpha., .beta.-Unsaturated Ketones Promoted by Lanthanoid Complexes," *J. Am. Chem. Soc.*, 1997, 119:2329-2330.
Brinkley, Michael "A Brief Survey of Methods for Preparing Protein Conjugates with Dyes, Haptens, and Cross-Linking Reagents", *Bioconjug. Chem* 3:2-13, 1992.
Brittain et al. "Physical Characterization of Pharmaceutical Solids," *Pharmaceutical Research*, 8(8):963-973, 1991.

Brown et al., "Selective Reductions. 37. Asymmetric Reduction of Prochiral Ketones with .beta.-(3-Pinanyl)-9borabicyclo[3.3.1]nonane," *J. Org. Chem.*, 1985, 50:1384-94.
Byrn et al., "Pharmaceutical Solids: A Strategic Approach to Regulatory Considerations," *Pharm. Res.*, 1995, 12(7):945-954.
Caira, "Crystalline Polymorphism of Organic Compounds," *Topics in Current Chemistry*, 1998, 198:163-208.
Cancer [online], [retrieved on Jul. 6, 2007] Retrieved from the Internet, URL: http://www.nlm.nih.gov/medlineplus/cancer.html.
Cascio et al., "26S proteasomes and immunoproteasomes produce mainly N-extended versions of an antigenic peptide", *EMBO J*, 20:2357-2366, 2001.
Center for Drug Evaluation and Research, Application No. 21-602, Medical Review, Clinical NDA Review, "NDA 21-602 Velcade TM (bortexomib) for injection," *Clinical Review*, 81-125, 2003.
Center for Drug Evaluation and Research, Application No. 21-602, Medical Review, Clinical NDA Review, "NDA 21-602 VelcadeTM (bortexomib) for injection," *Clinical Review*, 1-34, 2003.
Center for Drug Evaluation and Research, Application No. 21-602, Medical Review, Clinical NDA Review, "NDA 21-602 VelcadeTM (bortexomib) for injection," *Clinical Review*, 1-47, 2003.
Ciechanover, "The Ubiquitin-Proteasome Proteolytic Pathway," *Cell*, 1994, 79:13-21.
Cohen, "AIDS Mood Upbeat—For a Change," *Science*, 1995, 267:959-960.
Collins, Tucker, "Endothelial nuclear factor—KB and the initiation of the atherosclerotic lesion", *Lab. Invest.* 68(5), 499-508, 1993.
Concise Encyclopedia Chemistry, 1993, p. 490.
Corey et al., "A General, Catalytic, and Enantioselective Synthesis of .alpha.-Amino Acids," *J. Am. Chem. Soc.*, 1992, 114:1906-1908.
Corey et al., "Highly Enantioselective Borane Reduction of Ketones Catalyzed by Chiral Oxazaborolidines. Mechanism and Synthetic Implications," *J. Am. Chem. Soc.*, 1987, 109:5551-3.
Craiu et al. "Lactacystin and clasto-lactacystin13-lactone modify multiple proteasome 13-subunits and inhibit intracellular protein degradation and major hisotcompatibility complex class I antigen presentation" *J. Biol. Chem.* 272(20), 13437-13445, May 16, 1997.
Dana et al., "A Stereoselective Route to Hydroxyethylamine Dipeptide Isosteres," *J. Am. Chem. Soc.*, 2000, 65:7609-7611.
Dasmahapatra et al., "Carfilzomib Interacts Synergistically with Histone Deacetylase Inhibitors in Mantle Cell Lymphoma Cells In Vitro and In Vivo," *Mol. Cancer. Ther.*, 2011, 10:1686-1697.
Demo et al., "Antitumor Activity of PR-171, a Novel Irreversible Inhibitor of the Proteasome," *Cancer Research*, 2007, 67(13):6383-6391.
Dess et al., "A Useful 124-5 Triacetoxyperiodinane (the Dess-Martin Periodinane) for the Selective Oxidation of Primary or Secondary Alcohols and a Variety of Related 124-5 Species," *J. Am. Chem. Soc.*, 1991, 113:7277-7287.
Dess et al., "Readily Accessible 124-5 Oxidant for the Conversion of Primary and Secondary Alcohols to Aldehydes and Ketones," *J. Org. Chem.*, 1983, 48:4155-4156.
Diaz-Hernandez et al., "Neuronal Induction of the Immunoproteasome in Huntington's Disease" *J. Neurosci.*, 23:11653-1161, 2003.
Dimopoulos et al. "Lenalidomide plus Dexamethasone for Relapsed or Refractory Multiple Myeloma," *N Engl J Med.*, 2007, 357(21):2123-2132.
Dimopoulos et al., The role of novel drugs in multiple myeloma, *Ann. Oncol.*, 19 Suppl 7:vii121-7 (2008).
Dimopoulos, M. A. et al., Effect of Carfilzomib, Lenalidomide, and Dexamethasone VS Lenalidomide and Dexamethasone in Patients With Relapsed Multiple Myeloma by Line of Therapy: Secondary Analysis from an Interim Analysis of the Phase 3 Study ASPIRE (NCT01080391), presented at the 2015 American Society of Clinical Oncology Annual Meeting; May 29-Jun. 2, 2015; Chicago, Illinois, united States.
Dimopoulos, M. A. et al., Effect of Carfilzomib, Lenalidomide, and Dexamethasone VS Lenalidomide and Dexamethasone in Patients With Relapsed Multiple Myeloma by Line of Therapy: Secondary Analysis from an Interim Analysis of the Phase 3 Study ASPIRE (NCT01080391), presented at the 5th Annual Updates on Hematology and Oncology; Aug. 28-29, 2015; Bangkok, Thailand.

(56) References Cited

OTHER PUBLICATIONS

Dobler, "Total synthesis of (+)-epopromycin B and its analogues—studies on the inhibition of cellulose biosynthesis," *Tetrahedron Letters*, 2001, 42(2):215-218.
Egerer et al., "Tissue-Specific Up-Regulation of the Proteasome Subunit beta5i (LMP7) in Sjogren's Syndrome" *Arthritis Rheum* 54:1501-8, 2006.
Elliott et al., "The Proteasome a New Target for Novel Drug Therapies," *Am J Clin Pathol.*, 2001, 116:637-646.
Elofsson et al., "Towards subunit-specific proteasome inhibitors: synthesis and evaluation of peptide .alpha.',.beta.'-epoxyketones," *Chemistry & Biology*, 1999, 6:811-822.
European Search Report, EP 08 16 4241, completed Jan. 22, 2009, 5 pages.
European Search Report, EP 09 00 6228, completed Aug. 25, 2009, 7 pages.
European Search Report, EP 09822636.8, dated Aug. 1, 2012, 6 pages.
Extended European Search Report, EP 12189466.1, dated Jul. 23, 2013, 10 pages.
Extended European Search Report, EP 13167148.9, dated Aug. 2, 2013, 7 pages.
Extended European Search Report, European Application No. 14171395.8, dated Sep. 30, 2014.
Favit et al. "Prevention of13-Amyloid Neurotoxicity by Blockade of the Ubiquitin-Proteasome Protealytic Pathway", *J. Neurochem.* 75(3):1258-1263, 2000.
FDA mulls drug to slow late-stage Alzheimers[Online], [retrieved on Sep. 23, 2003]. Retrieved from the internet, URL: http://www.cnn.com/2003/HEALTH/conditions/09/24/alzheimers.drug.ap/index.html>.
Fenteany et al. "A 13-lactone related to lactacystin induces neurite outgrowth in a neuroblastoma cell line and inhibits cell cycle progression in an osteosarcoma cell line", *Pros. Natl. Acad. Sci. USA*, 91:3358-3362, Apr. 1994.
Figueiredo-Pereira et al., "The antitumor drug aclacinomycin A, which inhibits the degradation of ubiquitinated proteins, shows selectivity for the chymotrypsin-like activity of the bovine pituitary 20 S proteasome." *J. Biol. Chem.* 271: 16455-9 (1996).
First Vitality (2008, updated) Alzheimer's & Senile Dementia, http://www.1stvitality.co.uk/health/alzheimers/carnosine_proteasomal_alzheimers.htm, p. 1.
Fox et al. "Organic Chemistry", Publisher: Jones & Bartlett Pub, Published Jun. 15, 2004, Sec. 5-6, pp. 177-178, ISBN-10: 0763721972, ISBN-13: 9780763721978.
Gan et al., "Identification of Cathepsin B as a Mediator of Neuronal Death Induced by A—activated Microglial Cells Using a Functional Genomics Approach" *J. Biol. Chem.* 279:5565-5572, 2004.
Gao et al. "Inhibition of ubiquitin-proteasome pathway-mediated IKBa degradation by a naturally occurring antibacterial peptide" *J. Clin. Invest.* 106:439-448, 2000.
Garcia-Echeverria, "Peptide and Peptide-Like Modulators of 20S Proteasome Enzymatic Activity in Cancer Cells", *International J. of Peptide Res. and Ther.*, 12(1):49-64, Mar. 1, 2006.
Garrett et al., "Selective inhibitors of the osteoblast proteasome stimulate bone formation in vivo and in vitro," *J Clinical Investigation*, 2003, 111:1771-1782.
Gennaro, "Remington: Practice of the Science of Pharmacy," 19th Edition, 1995, Mack Publishing Company, Chapter 83, pp. 1447-1462.
Golub et al., "Molecular Classification of Cancer: Class Discovery and Class Prediction by Genes Expression Monitoring," *Science*, 1999, 286:531-537.
Gonzales et al. "Pain relief in chronic pancreatitis by pancreaticojejunostomy. An institutional experience" *Arch. Med. Res.* 28(3), 387-390, 1997.
Gordon et al. "1207 Results of study PX-171-007 a phase lb/2 study of carfilzomib, a selective proteasome inhibitor, in patients with selected advanced metastatic solid tumors" *Eur. Journ. of Cancer.* Supplement, 7(2):122-123, Sep. 2009.
Graz University of Technology, "Database of Fluorescent Dyes Properties and Applications" WWW.Fluorophonres.org, 33 pgs, Exhibit B to response filed with US Patent office dated Sep. 16, 2008 for U.S. Appl. No. 11/254,541 (now abandoned).
Green et al. "Protective Groups in Organic Synthesis", 2nd ed., Wiley & Sons, Inc., New York (1991).
Griffith et al. "Molecular recognition of angiogenesis inhibitors fumagillin and ovalicin by methionine aminopeptidase", *Proc. Natl. Acad. Sci. USA*, 95:15183-88, Dec. 1998.
Groettrup et al., "Selective proteasome inhibitors: modulators of antigen presentation?", *Drug Discovery Today*, 4(2):63-71, Feb. 1999.
Groll et al., "Crystal Structure of Epoxomicin:20S Proteasome Reveals a Molecular Basis for Selectivity of r0,a0-Epoxyketone Proteasome Inhibitors," *J. Am. Chem. Soc.* 2000, 122:1237-1238.
Gura, "Systems for Identifying New Drugs Are Often Faulty," *Science*, Nov. 7, 1997, 278(5340):1041-1042.
Hanada et aL, "Epoxomicin, A New Antitumor Agent of Microbial Origin", *The Journal of Antihiotics*, 45(11):1746-1752, Nov. 1992.
Hanson et al., Synthesis of New Dipeptide Hydroxyethylidene Isosteres via Grignard Chem., 1985, 50:5399-5401.
Harding et al., "Novel Dipeptide Aldehydes are Proteasome Inhibitors and Block the MHC-1 Antigen-Processing Pathway," *J. Immunology*, 1995, 155:1767-1775.
Hardy, "The secret life of the hair follicle," Trends in Genetics, 1992, 8:55-61.
Harris et al. "Effects of transforming growth factor 3 on bone nodule formation and expression of bone morphogenetic protein 2, osteocalcin, osteopontin, alkaline phosphatase, and type I collagen mRNA in long-term cultures of fetal rat calvarial osteoblasts", *J. Bone Miner. Res.* 9(6), 855-863, 1994.
Haugland, Rosaria "Coupling of Monoclonal Antibodies with Fluorophores", *Methods Mol. Biol.* 45, 205-221, 1995.
Hawley's Condensed Chemical Dictionary, 1993, p. 594.
Hilfiker, Ed., Polymorphism in the Pharmaceutical Industry, 2006, pp. 12-15.
Hoffman et al., Highly Stereoselective Chem., 2002, 67:1045-1056.
Holbeck et al.,"Analysis of Food and Drug Administration—Approved Anticancer Agents in the NC160 Panel of Human Tumor Cell Lines", *Mol Cancer Ther*, 9:1451-1460, May 4, 2010.
Huff, Joel R., "HIV Protease: A Novel Chemotherapeutic Target for Aids," *Journal of Medicinal Chemistry*, 34(8):2305-2314, Aug. 1991.
International Preliminary Report on Patentability for corresponding PCT Application No. PCT/US2005/012740, dated Oct. 19, 2006, 11 pgs.
International Preliminary Report on Patentability for corresponding PCT Application No. PCT/US2005/016335, dated Nov. 14, 2006, 11 pgs.
International Preliminary Report on Patentability for PCT/US2005/017000, dated Nov. 21, 2006, 12 pages.
International Preliminary Report on Patentability for PCT/US2005/028246, dated Feb. 6, 2007, 8 pages.
International Preliminary Report on Patentability for PCT/US2005/037966, dated Apr. 24, 2007, 12 pages.
International Preliminary Report on Patentability for PCT/US2005/044451, dated Jun. 13, 2007, 8 pages.
International Preliminary Report on Patentability for PCT/US2008/005997, dated Nov. 10, 2009, 7 pages.
International Preliminary Report on Patentability for PCT/US2008/011443, dated Apr. 7, 2010, 12 pages.
International Preliminary Report on Patentability for PCT/US2010/056395, dated May 24, 2012, 10 pages.
International Preliminary Report on Patentability for PCT/US2011/026629, dated Sep. 4, 2012, 11 pages.
International Preliminary Report on Patentability PCT/US2007/014427, dated Dec. 22, 2008, 8 pages.
International Preliminary Report on Patentability PCT/US2009/061498, dated May 5, 2011, 9 pages.
International Preliminary Report on Patentability PCT/US2011/031436, dated Oct. 9, 2012, 5 pages.
International Search Report (Partial) for PCT/US2008/011443, dated Dec. 9, 2008, 6 pages.

(56) References Cited

OTHER PUBLICATIONS

International Search Report and Written Opinion for corresponding PCT Application No. PCT/US2005/012740, dated Jan. 9, 2006, 16 pgs.
International Search Report and Written Opinion for corresponding PCT Application No. PCT/US2005/016335, dated Jan. 2, 2006, 17 pgs.
International Search Report and Written Opinion for PCT/US2007/014427, dated Dec. 3, 2007, 12 pages.
International Search Report and Written Opinion for PCT/US2010/056395, dated Mar. 15, 2011, 10 pages.
International Search Report and Written Opinion for PCT/US2011/026629, dated Jun. 30, 2011, 18 pages.
International Search Report and Written Opinion for PCT/US2011/031436, dated Nov. 28, 2011, 5 pages.
International Search Report and Written Opinion of the International Searching Authority for PCT/US2005/017000, dated Feb. 3, 2006, 12 pages.
International Search Report and Written Opinion of the International Searching Authority for PCT/US2005/028246, dated Jan. 19, 2006, 11 pages.
International Search Report and Written Opinion of the International Searching Authority for PCT/US2005/037966, dated Jan. 24, 2006, 17 pages.
International Search Report and Written Opinion of the International Searching Authority for PCT/US2005/044451, dated May 2, 2006, 12 pages.
International Search Report and Written Opinion of the International Searching Authority for PCT/US2006/043503, dated Feb. 19, 2007, 17 pages.
International Search Report and Written Opinion of the International Searching Authority for PCT/US2008/005997, dated Nov. 7, 2008, 8 pages.
International Search Report and Written Opinion of the International Searching Authority for PCT/US2008/011443, dated Mar. 25, 2009, 16 pages.
International Search Report and Written Opinion of the International Searching Authority for PCT/US2010/028126, dated Jun. 9, 2010, 13 pages.
International Search Report and Written Opinion of the International Searching Authority for PCT/US2012/055127, dated Dec. 18, 2012, 10 pages.
International Search Report and Written Opinion of the International Searching Authority for PCT/US2013/040127, dated Oct. 22, 2013, 15 pages.
International Search Report for PCT/US2009/061498, dated Dec. 10, 2009, 5 pages.
Iqbal et al. "Potent Inhibitors of Proteasome", J. Med Chem. 38:2276-2277, 1995.
Iqbal et al., "Potent .alpha.-ketocarbonyl and boronic ester derived inhibitors of proteasome," Bioorganic & Medicinal Chemistry Letters, 1996, 6:287-290.
Ivancsits et al., The proteasome inhibitor PR-171 inhibits cell growth, induces apoptosis, and overcomes de novo and acquired drug resistance in human multiple myeloma cells, Blood, ASH Annual Meeting Abstracts, 106:Abstract 1575 (2005).
Ivanisevic et al. ("Uses of X-Ray Powder Diffraction in the pharmaceutical Industry," Pharmaceutical Sciences Encyclopedia: Drug Discovery, Development, and Manufacturing, Edited by Shayne C. Gad, 2010, pp. 1-42.
Jacobsen et al., "Asymmetric Dihydroxylation via Ligand-Accelerated Catalysis," J. Am. Chem. Soc., 1988, 110:1968-1970.
Jain et al., "Emerging role of carfilzomib in treatment of relapsed and refractory lymphoid neoplasms and multiple myeloma," Core Evidence, pp. 43-57 (Apr. 2011).
Jain, "Delivery of Molecular Medicine to Solid Tumors," Science, 1996, 271(5252)1079-1080.
Jones et al., "Total Synthesis of the Immunosuppressant (-)-FK-506," J. Am. Chem. Soc., 1989, 111:1157-1159.

Jung et al. "Melatonin in cancer management: progress and promise" Cancer Res., 66(22):9789-9793, 2006.
Kessler et al. "Extended peptide-based inhibitors efficiently target the proteasome and reveal overlapping specificities of the catalytic 13-subunits", Chem & Biol. 8(9), 913-929, Aug. 8, 2001.
Khan et al "Immunoproteasomes Largely Replace Constitutive Proteasomes During an Antiviral, and Antibacterial Immune Response in the Liver" J Immunol5 167:6859-6868, 2001.
Kijima et al., Trapoxin, an antitumor cyclic tetrapeptide, is an irreversible inhibitor of mammalian histone deacetylase J. Biol. Chem., 268(3):22429-35, 1993.
Kim et al., "Proteasome inhibition by the natural products epoxomicin and dihydroeponemycin: insights into specificity and potency," Bioorganic & Medicinal Chemistry Letters, 1999, 9:3335-40.
Kisselev et al., "Proteasome inhibitirs: from research tools to drug candidates", Chemistry and Biology, 8(8):739-758, 2001.
Kojima et al., "Two-way cleavage of l3-amyloid protein precursor by multicatalytic proteinase" Fed. Eur. Biochem. Soc. 304:57-60, Jun. 1992.
Koong et al. Hypoxia causes the activation of nuclear factor-kB through the phosphorylation of IKBa on tyrosine residues , Cancer Research, 54:1425-1430, Mar. 15, 1994.
Koong et al. Hypoxic activation of nuclear factor-KB is mediated by a Ras and Raf signaling pathway and does not involve MAP kinase (ERK1 or ERK2)1, Cancer Research, 54:5273-5279, Oct. 15, 1994.
Kreidenweiss et al. "Comprehensive study of proteasome nhibitors against Plasmodium falciparum laboratory strains and field isolates from Gabon", Malar J., 7(187):1-8, 2008.
Krise et al. "A Novel Prodrug Approach for Tertiary Amines: Synthesis and Preliminary Evaluation of N-Phosphonooxymethyl Prodrugs", J. Med. Chem. 42:3094-3100, 1999.
Kuhn et al.: "Potent activity of carfilzomib, a novel, irreversible inhibitor of the ubiquitin-proteasome pathway, against preclinical models of multiple myeloma", Blood, 110(9): 3281-3290 prepublished online: Jun. 25, 2007.
Kumatori et al., "Abnormally high expression of proteasomes in human leukemic cells," Proc. Natl. Acad. Sci. USA, 1990, 87:7071-7075.
Kyprolis (carfilzomib), Highlights of Prescribing Information, Onyx Pharmaceuticals, Inc., an Amgen Inc. Subsidiary, Jul. 2015.
Kyprolis Prescribing Information, Revised Jul. 2012, 22 pages.
Lala et al., "Role of notric oxide in tymor progression: Lessons from experimental tumors," Cancer and Metastasis Reviews, 1998, 17:91-106.
Le Blanc et al., "Growth in Vivo and Prolongs Survival in a Murine Model Proteasome Inhibitor PS-341 Inhibits Human Myeloma Cell," Cancer Research, 2002, 62:4996-5000, Published online Sep. 1, 2002.
Lecker et al., "Multiple types of skeletal muscle atrophy involve a common program of changes in gene expression", FASEB J 18:39-51, 2004.
Lee et al., "Proteasome inhibitors: valuable new tools for cell biologists," Trends in Cell Biol., Oct. 1988, 8:397-403.
Liang et al., "Synthesis of Cryptophycin 52 Using the Sharpless Asymmetric Dihydroxylation: Diol to Epoxide Transformation Optimized for a Base-Sensitive Substrate," J. Am. Chem. Soc., 2000, 65:3143-3147.
Lin et al. "Alteration of substrate and inhibitor specificity of feline immunodeficiency virus protease", J. Virol., 74(10):4710-4720, 2000.
Loftsson et al., "Pharmaceutical Applications of Cyclodextrins. 1. Drug Solubilization and Stabalization," Journal of Pharmaceutical Sciences, American Pharmaceutical Association, 85(10)1017-1025 (1996).
Luke et al., "Review of the Basic and Clinical Pharmacology of Sulfobutylether-13-0Cyclodextrin(SBECD)," J. of Pharmaceutical Sciences, 2010, 99:3291-3301.
MacAry et al., "Mobilization of MHC class I molecules from late endosomes to the cell surface following activation of CD34-derived human Langerhans cells", PNAS 98:3982-3987, 2001.
Mandel et al. "Neuroprotective Strategies in Parkinson's Disease", CNS Drugs, 2003: 17(10); 729-62.

(56) References Cited

OTHER PUBLICATIONS

Marx et al., "Reactivity-Selectivity in the Swern Oxidation of Alcohols Using Dimethyl Sulfoxide-Oxalyl Chloride," J. Org. Chem., 1984, 49:788-793.
McGraw-Hill Dictionary of Chemical Terms, 1990, p. 282.
Meng et al., "Eponemycin Exerts its Antitumor Effect through the Inhibition of Proteasome Function," Cancer Research, 1999, 59:2798-2801.
Meng et al., "Epoxomicin, a potent and selective proteasome inhibitor, exhibits in vivo antimflamatory activity," Proc. Natl. Acad. Sci. USA, 1999, 96:10403-10408.
Merck Manual Breast Cancer, <<merckmanuals.com/home/womens_health_issues/breast_disorders/breast_cancer.html>>, accessed Aug. 24, 2015.
Merck Manual Colorectal Cancer , <<merckmanuals.com/home/skin_disorders/skin_cancer/melanoma.html?qt=melanoma&alt=sh>>, accessed Aug. 24, 2015.
Merck Manual Ovarian Cancer, <<merckmanuals.com/home/womens_health_issues/cancers_of_the_female_reproductive_system/ovarian_cancer.html>>, accessed Aug. 24, 2105.
Merck Manual Thyroid Cancers, <<merckmanuals.com/professional/endocrine_and_metabolic_disorders/thyroid_disorders/thyroid_cancer.html>>, accessed Aug. 24, 2015.
Merck Manuals Brain Tumors, <<http://www.merckmanuals.com/home/brain-spinal-cord-and-nerve-disorders/tumors-of-the-nervous-system/brain-tumors>>, accessed Aug. 24, 2015.
Min et al., "'Bortezomib in Combination with Conventional Chemotherapeutic Agents for Multiple Myeloma Compared with Bortezomib alone,'" Japanese Journal of Clinical Oncology, 2007, 37(12):961-968.
Mishto et al "Immunoproteasome and brains", Neurobiol. Aging, 27:54-66, LMP2 polymorphism in aged and Alzheimer's disease 2006.
Mitsiades et al., From the bench to the bedside: emerging new treatments in multiple myeloma, Best Pract. Res. Clin. Haematol., 20(4):797-816 (2007).
Molecular biology and biotechnology a comprehensive desk reference: Edited by R A Meyers. pp. 658-664. VCH, Weinheim, Germany, 1995, DM89 ISBN 1-56081-925-1.
Molecular Probes, Inc. , "Introduction to Fluorescence techniques", invitrogen detection technologies, 11 pgs, Molecular Probes, Inc. (2007), Exhibit A to response filed with US Patent Office dated Sep. 16, 2008 for U.S. Appl. No. 11/254,541 (now abandoned).
Morissette Sherry, et al. "high-thoughput crystallization: polymorphs, salts, co-crystals and solvates of pharmaceutical solids, advanced drug delivery reivews" Amsterdam, vol. 56, No. 3, 2004 p. 276.
Morris, "Structural Aspects of Hydrates and Solvates in Polymorphism in Pharmaceutical Solids", Polymorphism in Pharmaceutical Solids, Ed H. G. Nbrittain, Marcel Dekker, New York, pp. 125-181 (1999).
Muchamuel et al., "A selective inhibitor of the immunoproteasome subunit NMP7 blocks cytokine production and attenuates progression of experimental arthritis," Nature Med., Jun. 2009, 15:781-787.
Myung et al., "Lack of Proteasome Active Site Allostery as Revealed by Subunit-Specific Inhibitors," Molecular Cell, 2001, 7(2):411-420.
Myung et al., The Ubiquitin-Proteasome Reviews, 2001, 21(4):245-273.
Nemoto et al., "Catalytic Asymmetric Epoxidation of Enones Using La-BINOL-Triphenylarsine Oxide Complex: Structural Determination of the Asymmetric Catalyst," J. Am. Chem. Soc., 2001, 123:2725-2732.
Newman et al. "Solid-state analysis of the active pharmaceutical ingredient in drug products," Drug Discovery Today, 8(19):898-905, 2003.
Oishi et al., "Diastereoselective synthesis of new psi '(E)-CH=CMel- and psi'(Z)-CH=CMel-type alkene dipeptide isosteres by organocopper reagents and application to conformationally restricted cyclic RGD peptidomimetics," J. Org. Chem., 2002, 67:6162-6173.
Orlowski and Kuhn, "Proteasome Inhibitors in Cancer Therapy: Lessons from the First Decade," Clin. Canc. Res., 2008, 14:1649-165.
Orlowski et al., "Phase I Trial of the Proteasome Inhibitor PS-341 in Patients With Refractory Hematologic Malignancies," Journal of Clinical Oncology, 2002, 20(22):4420-4427.
Overkleeft et al. "Solid phase synthesis of peptide vinyl sulfone and peptide expoxyketone proteasome inhibitors", Tetrahedron Letters, 41(32), 6005-6009, 2000.
Palombella et al., "The Ubiquitin-Proteasome Pathway is Required for Processing the NF-.kappa.B1 Precursor Protein and the Activation of NF-.kappa.B," Cell, 1994, 78:773-785.
Paoluzzi et al., "Targeting Bcl-2 family members with the BH3 mimetic AT-101 markedly enhances the therapeutic effects of chemotherapeutic agents in in vitro and in vivo models of B-cell lymphoma", Blood, 111(11):5350-5358, 2008.
Paugam et al., "Characterization and role of protozoan parasite proteasomes," Trends Parasitol., 2003, 19:55-59.
Pivazyan et al., "Inhibition of HIC-1 Protease by a Boron-Modified Polypeptide", Biochem. Pharm. 60:927-936, Mar. 2000.
Polymorphism in Pharmaceutical Solids, edited by Brittain, 1999, Marcel Dekker Inc., p. 228-229, 236.
Pye et al. "Proteasome inhibition ablates activation of NF-KB in myocardial reperfusion and reduces reperfusion of injury", Am. J. Physiol. Heart Circ. Physiol 284:H919-H926, 2003.
Qureshi et al., "The Proteasome as a Lipopolysaccharide-Binding Protein in Macrophages: Differential Effects of Proteasome Inhibition on Lipopolysaccharide-Induced Signaling Events," J. Immunology, 2003, 171:1515-1525.
Raw et al. "Regulatory considerations of pharmaceutical solid polymorphism in Abbreviated New Drug Applications (ANDAs)," Advanced Drug Delivery Reviews 56:397-414, 2004.
Reidlinger et al. "Catalytic Properties of 26 S and 20 S Proteasomes and Radiolabling of MB 1, LMP7, and C7 Subunits Associated with Trypsin-like and Chymotrypsin-like Activities", J. of Biol Chem. 272(40), 24899-24905, May 27, 1997.
Roccaro et al., "Selective inhibition of chymotrypsin-like activity of the immunoproteasome and constitutive proteasome in Waldenstrom macroglobulimia," Blood, 2010, 115:4051-4060.
Rossi et al., "Proteasome inhibitors in cancer therapy: death by indigestion," Cell Death and Differentiation, 2005, as:1255-1257.
Rouhi, Chemical & Engineering News, Feb. 24, 2004, p. 32-35.
Safadi et al., "Phosphoryloxymethyl Carbarnates and Carbonates—Novel Water-Soluble Prodrugs for Amines and Hindered Alcohols", Pharmaceutical Research 10(9), 1350-1355, Mar. 2, 1993.
Schwarz et al., 'The Selective Proteasome Inhibitors Lactacystin and Epoxomicin Can Be Used to Either Up- or Down-Regulate Antigen Presentation at Nontoxic Doses', The Journal of Immunology, 164: 6148-6157, 2000.
Shah et al. "Analytical Techniques for Quantification of Amorphous/Crystalline Phases in Pharmaceutical Solids," Journal of Pharm. Sciences, 95(8):1641-1665, 2006.
Shao et al., "A New Asymmetric Synthesis of .alpha.-Methylcysteines via Chiral Aziridines," J. Org. Chem., 1995, 60:790-791.
Sharpless et al., "High Stereo- and Regioselectivities in the Transition Metal Catalyzed Epoxidations of Olefinic Alcohols by tert-Butyl Hydroperoxide," J. Am. Chem. Soc., 1973, 95:6136-6137.
Shoemaker, "The NCI60 human tumour cell line anticancer drug screen",Cancer, Nature Reviews, 6:813-823, Oct. 2006.
Simsek et al. "Hepatitis B Virus Large and Middle Glycoproteins are Degraded by a Proteasome Pathway in Glucosidase-Inhibited Cells but Not in Cells with Functional Glucosidase Enzyme", J. Virol. 79(20), 12914-12920, Oct. 2005.
Sin et al., "Eponymycin analogues: syntheses and use as probes of angiogenesis," Bioorganic & Medicinal Chemistry Letters, 6(8):1209-1217, Aug. 1998.
Sin et al., "Total synthesis of the potent proteasome inhibitor epoxomicin: a useful tool for understanding proteasome biology," Bioorganic & Medicinal Chemistry Letters, 1999, 9:2283-2288.
Singhal et al. "Drug polymorphism and dosage form design: a practical perspective" Advanced Drug Delivery Reviews, 56:335-347, 2004.

(56) References Cited

OTHER PUBLICATIONS

Spaltenstein et al., "Design and Synthesis of Novel Protease Inhibitors. Tripeptide .alpha.',.beta.'-Epoxyketones as Nanomolar Inactivators of the Proteasome," Tetrahedron Letters, 1996, 37:1343-6.
Stahl and Wermuth, Handbook of Pharmaceutical Salts: Properties, Selection, and Use, 2002, pp. 198-200.
Stein et al., "Kinetic Characterization of the Chymotryptic Activity of the 20S Proteasome," Biochemistry, 1996, 35:3899-3908.
Sterz et al., The potential of proteasome inhibitors in cancer therapy, Expert Opin. Investig. Drugs, 17(6):879-95 (2008).
Stewart, A. K. et al., Interim Results From the Randomized, Open-Label, Multicenter, Phase 3 Aspire Study, Evaluating Carfilzomib, Lenalidomide, and Dexamethasone (KRD) VS Lenalidomide and Dexamethasone (RD) in Patients With Relapsed Multiple Myeloma (RMM), presented at the 5th Emirates Haematology Conference; Mar. 19-21, 2015; Dubai, United Arab Emirates.
Stewart, A. K. et al., Superior Health-Related Quality of Life With Carfilzomib, Lenalidomide, and Dexamethasone Versus Lenalidomine and Dexamethasone in Patients With Relapsed Multiple Myeloma: Results from the ASPIRE Trial, presented at the 2015 International Myeloma Workshop, Sep. 23-26, 2015; ROme, Italy.
Stoklosa et al. "Prospects for p53-based cancer therapy", Acta Biochim Pol., 52(2): 321-328, 2005.
Strickley, Robert G., "Solubilizing Excipients in Oral and Injectable Formulations," Pharmaceutical Research, 21(2):201-230 (2004).
Sun et al inhibition of acute graft-versus-host disease with retention of graft-versus-tumor effects by the proteasome inhibitor bortezomib: PNAS, 101(21):8120-8125, (2004).
Szalay et al. "Ongoing coxsackievirus myocarditis is associated with increased formation and activity of myocardial immunoproteaseomes", Am. J. Pathol. 168(5), 1542-1552, May 2006.
Tawa et al., "Inhibitors of the Proteasome Reduce the Accelerated Proteolysis in Atrophying Rat Skeletal Muscles", JCI 100:197-203, 1997.
Terato et al. "Induction of arthritis with monoclonal antibodies to collagen" J Immunol, 148(7), 2103-2108, Apr. 1, 1992.
Thanos et al., "NF-.kappa.B: A Lesson in Family Values," Cell, 1995, 80:529-532.
Thompson., "Cyclodextrins-enabling excipients: their present and future use in pharmaceuticals," Critical Reviews in Therapeutic Drug Carrier Systems, 14(1):1-104 (1997).
Tong, Wei-Qin (Tony), "Applications of Complexation in the Formulation of Insoluble Compounds," R. Liu, Ed., pp. 111-139 (2000).
Traenckner et al., "A proteasome inhibitor prevents activation of NF-.kappa.B and stabilizes a newly phosphorylated form of I.kappa.B-.alpha. that is still bound to NF-.kappa.B," EMBO J., 1994, 13:5433-5441.
Tu et al., "An Efficient Assymettric Epoxidation Method for trans-Olefins Mediated by a Fructose-Derived Ketone," J. Am. Chem. Soc., 1996, 118:9806-9807.
U.S. Pharmacopia #23, National Formulary #18 (1995), p. 1843-1844.
Ubiquitinated Proteins, Shows Selectivity for the Chymotrypsin-like Activity of the Bovine Pituitary 20 S Proteasome, The Journal of Biological Chemistry, 271(2):16455-16459, Jul. 1996.

Vogel's textbook of practical organic chemistry, 5th Ed. See p. 135, "2.20 Recrystallisation Techniques" and p. 141, 2nd paragraph onwards, Feb. 1996.
Voskoglou-Nomikos, "Clinical Predictive Value of the in Vitro Cell Line, Human Xenograft, and Mouse Allograft Preclinical Cancer Models," Clin Cancer Res., 2003, 9(11):4227-4239.
Wang et al., "A New Type of Ketone Catalyst for Asymmetric Epoxidation," J. Org. Chem., 1997, 62:8622-8623.
Watanabe et al. "Synthesis of boronic acid derivatives of tyropeptin: Proteasome inhibitors", Bioorg. & Med. Chem., 19(8):2343-2345, Apr. 2009.
WebMD "HIV and Aids", www.webmd.com/hiv-aids/guide/sexual-health-aids pp. 1-2, 2009, updated.
Wilson et al., "Novel disease targets and management approaches for diffuse large B-cell lymphoma", Leukemia & Lymphoma, 51 suppl. 1:1-10 abstract only, 2010.
Wipf et al., "Methyl- and (Trifluoromethyl)alkene Peptide Isosteres: Synthesis and Evaluation of Their Potential as .beta.-Turn Promoters and Peptide Mimetics," J. Org. Chem., 1998, 63:6088-6089.
Xu et al. "Mutations in the tumor suppressors Smad2 and Smad4 inactivate transforming growth factor 3 signaling by targeting Smads to the ubiquitin-proteasome pathway", PNAS 97(9), 4820-4825, Apr. 25, 2000.
Yang et al., "Pharmacokinetics, Pharmacodynamics, Metabolism, Distribution, and Excretion of Carfilzomib in Rats," Drug Metabol. and Disposition, 2011, 39:1873-1882.
Yu et al. "The Ubiquitin-Proteasome System Facilitates the Transfer of Murine Coronavirus from Endosome to Cytoplasm during Virus Entry", J. Virol. 79(1), 644-648, Jan. 2005.
Zhou et al., "Design and Synthesis of an Orally Bioavailable and Selectrive Peptide Epoxyketone Proteasome Inhibitor (PR-047)," J. Med. Chem., 2009, 52 (9):3028-3038.
Zhu et al., "3D-QSAR studies of boron-containing dipeptides as proteasome inhibitors with CoMFA and CoMSIA methods", Eur Journ. Med. Chem., 44(4):1486-1499, Apr. 2009.
Zhu et al., "Design Synthesis and biological evaluation of tripeptide boronic acid proteasome inhibitors", Bioorg & Med. Chem., 17(19):6851-6861, Oct. 2009.
Zollner et al. "Proteasome inhibition reduces superantigen-mediated T cell activation and the severity of psoriasis in a SCID-hu model", J. Clin. Invest., 109(5): 671-679, 2002.
USFDA Guidance for Industry Process Validation: General Principles and Practices, Published in Jan. 2011 Current Good Manufacturing Practices (CGMP).
Niesvizky et al., 9232: A phase lb multicenter dose escalation study of carfilzomib plus lenalidomide and low-dose dexamethasone in relapsed multiple myeloma—preliminary results. Eur. J. Cancer Suppl. 7(2): 569 (2009).
Jagannath et al., Initial results of PX-171-003, an open label, single-arm, phase II study of carflizomib (CFZ) in patients with relapsed and refractory multiple myeloma (MM), Blood, 112:864 (2008).
Richardson et al., Lenalidomide, bortezomib, and dexamethasone (Rev/Vel/Dex) in patients with relapsed or relapsed/refractory multiple (MM): Preliminary results of a phase II study, Biosis, Database Accession No. PREV200800217986 (2007).
Vu et al., Initial results of PX-171-004, an open label, single arm, phase II study of carfilzomib (CFZ) in patients with relapsed myeloma (MM), Blood, 112: 865 (2008).

\* cited by examiner

A.

| Cohort | CFZ / LEN (mg/m2/mg) | N | VGPR | PR | MR | SD | PD |
|---|---|---|---|---|---|---|---|
| 1 | 15/10 | 6 | 2 | 1 |  | 2 | 1 |
| 2 | 15/15 | 4 | 1 | 1 | 1 | 1 |  |
| 3 | 15/20 | 7 | 2 | 3 |  | 2 |  |

B.

*nCR: IFE Positive  **Off Study

COMBINATION THERAPY WITH PEPTIDE EPOXYKETONES

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multi-catalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell division, and NF-κB activation.

The 20S proteasome is a 700 kDa cylindrical-shaped multicatalytic protease complex comprised of 28 subunits organized into four rings that plays important roles in cell growth regulation, major histocompatibility complex class I presentation, apoptosis, antigen processing, NF-κB activation, and transduction of pro-inflammatory signals. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three γ-interferon-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

SUMMARY OF THE INVENTION

One aspect of the invention relates to combination therapy, wherein a peptide epoxyketone or a pharmaceutically acceptable salt thereof is administered with one or more other therapeutic agents and the combination shows efficacy that is greater than the efficacy of either agent being administered alone (e.g., synergistic or additive antitumor effect). Such combination treatment may be achieved by way of the simultaneous, sequential, or separate dosing of the individual components of the treatment.

Another aspect of the invention relates to methods for the treatment of cancer, comprising administering a peptide epoxyketone with one or more other therapeutic agents and the combination shows efficacy that is greater than the efficacy of either agent being administered alone (e.g., synergistic or additive antitumor effect). Such combination treatment may be achieved by way of the simultaneous, sequential, or separate dosing of the individual components of the treatment.

Another aspect of the invention relates to methods for the treatment of autoimmune diseases, comprising administering a peptide epoxyketone with one or more other therapeutic agents and the combination shows efficacy that is greater than the efficacy of either agent being administered alone (e.g., synergistic or additive antitumor effect). Such combination treatment may be achieved by way of the simultaneous, sequential, or separate dosing of the individual components of the treatment.

In certain embodiments, the one or more other therapeutic agent is selected from an HDAC inhibitor, an antibiotic, a taxane, an antiproliferative/antimitotic alkylating agents, a platinum coordination complex, a steroid, an immunomodulator, a topoisomerase inhibitor, an m-TOR inhibitor, and protein kinase inhibitor.

DETAILED DESCRIPTION OF THE INVENTION

Figure 1:
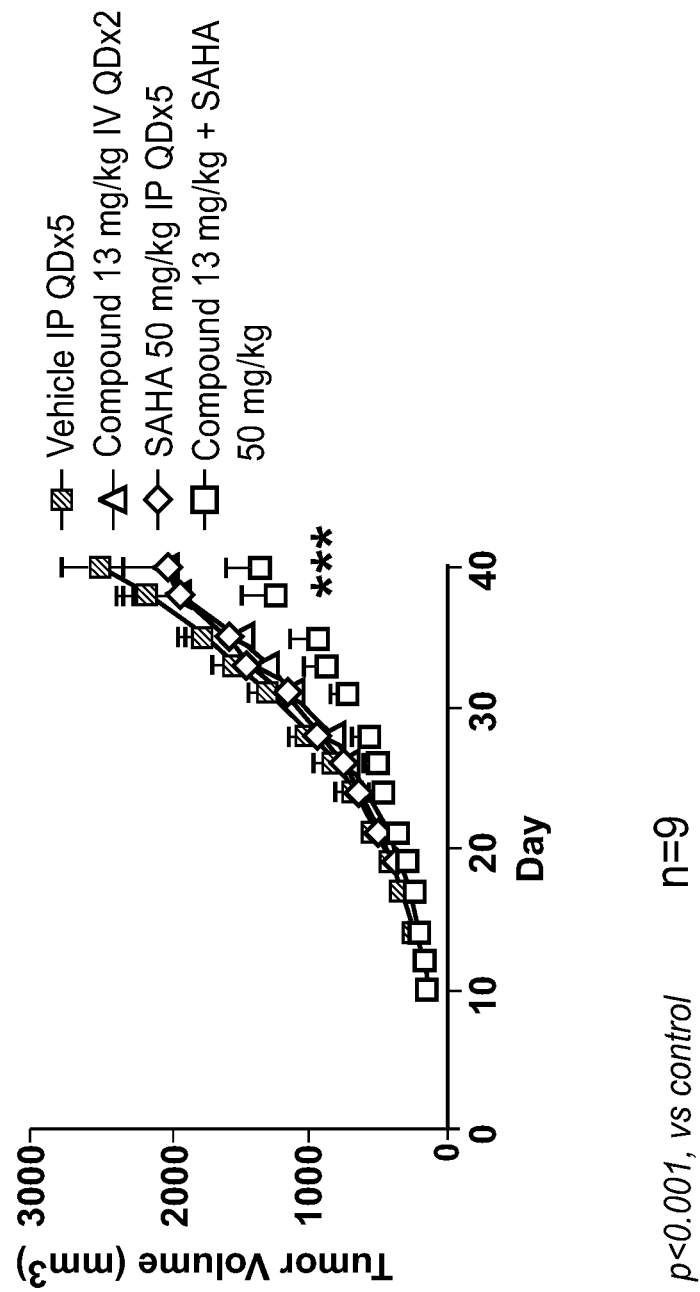
FIG. 1 shows a graph of tumor volume over time for mice treated with vehicle, Compound 1, SAHA, or Compound 1 in combination with SAHA after RL cell tumors had reached about 50 mm$^3$ in size.

In certain embodiments, the peptide epoxyketone is selected from a compound of any one of groups 1 to 7. In each of the following groups, the values for various moieties (e.g., for $R^1$, etc.) are understood to be consistent within a group, but values for one group (e.g. Group 1) do not apply to another group.

Group 1

In one embodiment, the peptide epoxyketone has a structure of Formula (1) or a pharmaceutically acceptable salt thereof.

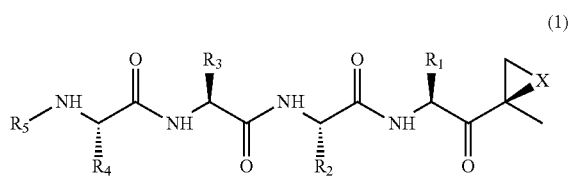

(1)

where X is oxygen, $R_1$, $R_2$, $R_3$ and $R_4$ are independently selected from the group consisting of branched or unbranched $C_{1-6}$ alkyl or branched or unbranched $C_{1-6}$ hydroxy alkyl or branched or unbranched $C_{1-6}$ alkoxy alkyl, aryl, and aryl-substituted branched or unbranched $C_{1-6}$ alkyl, wherein such groups can further include: amide linkages; amines; carboxylic acids and salts thereof; carboxyl esters, including $C_{1-5}$ alkyl esters and aryl esters; thiols and thioethers; and $R_5$ is a further chain of amino acids, hydrogen, acetyl, or a protecting group, such as N-terminal protecting groups known in the art of peptide synthesis, including t-butoxy carbonyl (BOC), benzoyl (Bz), fluoren-9-yl-methoxycarbonyl (Fmoc), triphenylmethyl(trityl) and trichloroethoxycarbonyl (Troc) and the like. The use of various N-protecting groups, e.g., the benzyloxy carbonyl group or the t-butyloxycarbonyl group (BOC), various coupling reagents, e.g., dicyclohexylcarbodiimide, 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HBT), and various cleavage reagents: for example, trifluoroacetic acid; HCL in dioxane; hydrogenation on Pd—C in organic solvents, such as methanol or ethyl acetate; boron tris(trifluoroacetate); and cyanogen bromide, and reaction in solution with isolation and purification of intermediates is well-known classical peptide methodology.

In some embodiments of chymotrypsin-like activity inhibitors, $R_1$ is branched or unbranched $C_{1-6}$ alkyl. In some embodiments of chymotrypsin-like activity inhibitors, $R_1$ is isobutyl. In some embodiments of chymotrypsin-like activity inhibitors, $R_2$ is branched or unbranched $C_{1-6}$ alkyl or aryl. In some embodiments of chymotrypsin-like activity inhibitors, $R_2$ is phenyl, phenylmethyl, or 1-naphthyl. In some embodiments of chymotrypsin-like activity inhibitors, $R_3$ is branched or unbranched $C_{1-6}$ alkyl or aryl. In some embodiments of chymotrypsin-like activity inhibitors, $R_3$ is isobutyl, phenyl or 1-naphthyl. In some embodiments of chymotrypsin-like activity inhibitors, $R_4$ is branched or unbranched $C_{1-6}$ alkyl, aryl, and aryl-substituted branched or unbranched $C_{1-6}$ alkyl. In some embodiments of chymotrypsin-like activity inhibitors, $R_4$ is isobutyl, phenyl, 1-naphthyl, phenylmethyl, or 2-phenylethyl. In some embodiments of chymotrypsin-like activity inhibitors, $R_5$ is hydrogen, $C_{1-6}$ alkanoyl, substituted or unsubstituted aryl, substituted or unsubstituted heteroaryl, where substituents include halogen, carbonyl, nitro, hydroxy, aryl, and $C_{1-5}$ alkyl. In some embodiments of chymotrypsin-like activity inhibitors, $R_5$ is hydrogen, acetyl, substituted or unsubstituted aryl.

In some preferred embodiments of chymotrypsin-like activity inhibitors, simultaneously, $R_1$ is isobutyl, $R_2$ is phenylmethyl, $R_3$ is isobutyl, and $R_4$ is 2-phenylethyl, and $R_5$ is acetyl. The peptide having such values is referred to herein as peptide (b).

In some embodiments of PGPH activity inhibitors, $R_1$ is hydrogen, branched or unbranched $C_{1-6}$ alkyl. In some embodiments of PGPH activity inhibitors, $R_1$ is isobutyl. In some embodiments of PGPH activity inhibitors, $R_2$ is hydrogen, branched or unbranched $C_{1-6}$ alkyl or aryl. In some embodiments of PGPH activity inhibitors, $R_2$ is phenyl, phenylmethyl, or 1-naphthyl. In some embodiments of PGPH activity inhibitors, $R_3$ is hydrogen, branched or unbranched $C_{1-6}$ cyclic alkylene bonded to the $R_3$ backbone unit. In some embodiments of PGPH activity inhibitors, $R_3$ is ethylene bonded to the amine of the $R_3$ amino acid backbone, such as would be the case for the amino acid proline. In some optional embodiments of PGPH activity inhibitors, $R_4$ is hydrogen, branched or unbranched $C_{1-6}$ alkyl, aryl, and aryl-substituted branched or unbranched $C_{1-6}$ alkyl. In some other optional embodiments of PGPH activity inhibitors, $R_4$ is hydrogen, or isopropyl. In some optional embodiments of PGPH activity inhibitors, $R_5$ is hydrogen, $C_{1-6}$ alkanoyl, substituted or unsubstituted aryl, substituted or unsubstituted heteroaryl, where substituents include halogen, carbonyl, monosubstituted-, disubstituted- or unsubstituted-amino, nitro, hydroxy, aryl, and $C_{1-5}$ alkyl. In some optional embodiments of PGPH activity inhibitors, $R_5$ is acetyl, N-acetyl-piperidinecarbonyl, N-dimethylaminobenzyl, isotonic, or benzoylbenzoic.

In some preferred embodiments of PGPH activity inhibitors, simultaneously, $R_1$ is isobutyl, $R_2$ is phenyl, $R_3$ is ethylene bonded to the $R_3$ amine of the amino acid backbone, and $R_4$ is hydrogen, and $R_5$ is acetyl.

Group 2

In certain embodiments, the peptide epoxyketone has a structure of Formula (2) or a pharmaceutically acceptable salt thereof,

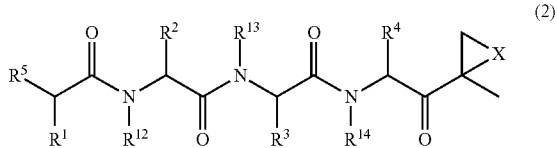

wherein each A is independently selected from C=O, C=S, and SO$_2$, preferably C=O; or A is optionally a covalent bond when adjacent to an occurrence of Z;

L is absent or is selected from C=O, C=S, and SO$_2$, preferably L is absent or C=O;

M is absent or is C$_{1-12}$alkyl, preferably C$_{1-8}$alkyl;

Q is absent or is selected from O, NH, and N—C$_{1-6}$alkyl, preferably Q is absent, O, or NH, most preferably Q is absent or O;

X is O;

Y is absent or is selected from O, NH, N—C$_{1-6}$alkyl, S, SO, SO$_2$, CHOR$^{10}$, and CHCO$_2$R$^{10}$;

each Z is independently selected from O, S, NH, and N—C$_{1-6}$alkyl, preferably O; or Z is optionally a covalent bond when adjacent to an occurrence of A;

R$^1$, R$^2$, R$^3$, and R$^4$ are each independently selected from optionally substituted C$_{1-6}$alkyl, C$_{1-6}$hydroxyalkyl, C$_{1-6}$alkoxyalkyl, aryl, and C$_{1-6}$aralkyl, wherein substituents may include, but are not limited to, one or more of amide, amine, carboxylic acid (or a salt thereof), ester (including C$_{1-5}$ alkyl ester and aryl ester), thiol, or thioether substituents;

R$^5$ is N(R$^6$)LQR$^7$;

R$^6$, R$^{12}$, R$^{13}$, and R$^{14}$ are independently selected from hydrogen, OH, C$_{1-6}$alkyl, and a group of Formula (3); preferably, R$^6$ is selected from hydrogen, OH, and C$_{1-6}$alkyl, and R$^{12}$, R$^{13}$, and R$^{14}$ are independently selected from hydrogen and C$_{1-6}$alkyl, preferably hydrogen;

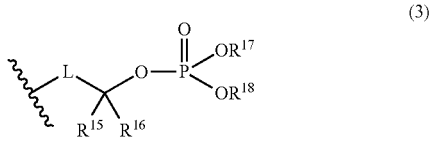

R$^7$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZAZ—C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, R$^8$ZAZ—C$_{1-8}$alkyl-ZAZ—C$_{1-8}$alkyl-, heterocyclylMZAZ—C$_{1-8}$alkyl-, (R$^8$O)(R$^9$O)P(=O)O—C$_{1-8}$alkyl-, (R$^{10}$)$_2$N—C$_{1-12}$alkyl-, (R$^{10}$)$_3$N$^+$—C$_{1-12}$alkyl-, heterocyclylM-, carbocyclylM-, R$^{11}$SO$_2$C$_{1-8}$alkyl-, and R$^{11}$SO$_2$NH; preferably C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—C$_{1-8}$alkyl-, (R$^8$O)(R$^9$O)P(=O)O—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH, wherein each occurrence of Z and A is independently other than a covalent bond; or R$^6$ and R$^7$ together are C$_{1-6}$alkyl-Y—C$_{1-6}$alkyl, C$_{1-6}$alkyl-ZAZ—C$_{1-6}$alkyl, ZAZ—C$_{1-6}$alkyl-ZAZ—C$_{1-6}$alkyl, ZAZ—C$_{1-6}$alkyl-ZAZ, or C$_{1-6}$alkyl-A, thereby forming a ring; preferably C$_{1-2}$alkyl-Y—C$_{1-2}$alkyl, C$_{1-2}$alkyl-ZA-C$_{1-2}$alkyl, A-C$_{1-2}$alkyl-ZA-C$_{1-2}$alkyl, A-C$_{1-3}$alkyl-A, or C$_{1-4}$alkyl-A, wherein each occurrence of Z and A is independently other than a covalent bond;

R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^8$ and R$^9$ together are C$_{1-6}$alkyl, thereby forming a ring;

each R$^{10}$ is independently selected from hydrogen and C$_{1-6}$alkyl, preferably C$_{1-6}$alkyl;

R$^{11}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl; R$^{15}$ and R$^{16}$ are independently selected from hydrogen and C$_{1-6}$alkyl, or R$^{15}$ and R$^{16}$ together form a 3- to 6-membered carbocyclic or heterocyclic ring; and R$^{17}$ and R$^{18}$ are independently selected from hydrogen, a metal cation, C$_{1-6}$alkyl, and C$_{1-6}$aralkyl, or R$^{17}$ and R$^{18}$ together represent C$_{1-6}$alkyl, thereby forming a ring;

provided that when R$^6$, R$^{12}$, R$^{13}$, and R$^{14}$ are H or CH$_3$, and Q is absent, LR$^7$ is not hydrogen, unsubstituted C$_{1-6}$alkylC=O, a further chain of amino acids, t-butoxycarbonyl (Boc), benzoyl (Bz), fluoren-9-ylmethoxycarbonyl (Fmoc), triphenylmethyl(tityl), benzyloxycarbonyl (Cbz), trichloroethoxycarbonyl (Troc); or substituted or unsubstituted aryl or heteroaryl; and in any occurrence of the sequence ZAZ, at least one member of the sequence must be other than a covalent bond.

In certain embodiments, when R$^6$ is H, L is C=O, and Q is absent, R$^7$ is not hydrogen, C$_{1-6}$alkyl, or substituted or unsubstituted aryl or heteroaryl. In certain embodiments, when R$^6$ is H and Q is absent, R$^7$ is not a protecting group such as those described in Greene, T. W. and Wuts, P. G. M., "Protective Groups in Organic Synthesis", John Wiley & Sons, 1999 or Kocieński, P. J., "Protecting Groups", Georg Thieme Verlag, 1994.

In some embodiments, R$^1$, R$^2$, R$^3$, and R$^4$ are selected from C$_{1-6}$alkyl or C$_{1-6}$aralkyl. In preferred embodiments, R$^2$ and R$^4$ are C$_{1-6}$alkyl and R$^1$ and R$^3$ are C$_{1-6}$aralkyl. In the most preferred embodiment, R$^2$ and R$^4$ are isobutyl, R$^1$ is 2-phenylethyl, and R$^3$ is phenylmethyl.

In certain embodiments, L and Q are absent and R$^7$ is selected from C$_{1-6}$alkyl, C$_{1-6}$alkenyl, C$_{1-6}$alkynyl, C$_{1-6}$aralkyl, and C$_{1-6}$heteroaralkyl. In certain such embodiments, R$^6$ is C$_{1-6}$alkyl and R$^7$ is selected from butyl, allyl, propargyl, phenylmethyl, 2-pyridyl, 3-pyridyl, and 4-pyridyl.

In other embodiments, L is SO$_2$, Q is absent, and R$^7$ is selected from C$_{1-6}$alkyl and aryl. In certain such embodiments, R$^7$ is selected from methyl and phenyl.

In certain embodiments, L is C=O and R$^7$ is selected from C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH—, wherein each occurrence of Z and A is independently other than a covalent bond. In certain embodiments, L is C=O, Q is absent, and R$^7$ is H.

In certain embodiments, R⁶ is $C_{1-6}$alkyl, R⁷ is $C_{1-6}$alkyl, Q is absent, and L is C=O. In certain such embodiments, R⁷ is ethyl, isopropyl, 2,2,2-trifluoroethyl, or 2-(methylsulfonyl)ethyl.

In other embodiments, L is C=O, Q is absent, and R⁷ is $C_{1-6}$aralkyl. In certain such embodiments, R⁷ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, R⁶ is $C_{1-6}$alkyl, and R⁷ is aryl. In certain such embodiments, R⁷ is substituted or unsubstituted phenyl.

In certain embodiments, L is C=O, Q is absent or O, n is 0 or 1, and R⁷ is —(CH₂)$_n$carbocyclyl. In certain such embodiments, R⁷ is cyclopropyl or cyclohexyl.

In certain embodiments, L and A are C=O, Q is absent, Z is O, n is an integer from 1 to 8 (preferably 1), and R⁷ is selected from R⁸ZA-$C_{1-8}$alkyl-, R¹¹Z—$C_{1-8}$alkyl-, R⁸ZA-$C_{1-8}$alkyl-ZAZ—$C_{1-8}$alkyl-, (R⁸O)(R⁹O)P(=O)O—$C_{1-8}$alkyl-ZAZ—$C_{1-8}$alkyl-, (R⁸O)(R⁹O)P(=O)O—$C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, R⁷ is heterocyclylMZAZ—$C_{1-8}$alkyl- where heterocyclyl is substituted or unsubstituted oxodioxolenyl or N(R¹²)(R¹³), wherein R¹² and R¹³ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, n is an integer from 1 to 8, and R⁷ is selected from (R⁸O)(R⁹O)P(=O)O—$C_{1-8}$alkyl-, (R¹⁰)₂N$C_{1-8}$alkyl, (R¹⁰)₃N⁺(CH₂)$_n$—, and heterocyclyl-M-. In certain such embodiments, R⁷ is —$C_{1-8}$alkylN(R¹⁰)₂ or —$C_{1-8}$alkylN⁺(R¹⁰)₃, where R¹⁰ is $C_{1-6}$alkyl. In certain other such embodiments, R⁷ is heterocyclylM-, where heterocyclyl is selected from morpholino, piperidino, piperazino, and pyrrolidino.

In certain embodiments, L is C=O, R⁶ is $C_{1-6}$alkyl, Q is selected from O and NH and R⁷ is selected from $C_{1-6}$alkyl, cycloalkyl-M, $C_{1-6}$aralkyl, and $C_{1-6}$heteroaralkyl. In other embodiments, L is C=O, R⁶ is $C_{1-6}$alkyl, Q is selected from O and NH, and R⁷ is $C_{1-6}$alkyl, where $C_{1-6}$alkyl is selected from methyl, ethyl, and isopropyl. In further embodiments, L is C=O, R⁶ is $C_{1-6}$alkyl, Q is selected from O and NH and R⁷ is $C_{1-6}$aralkyl, where aralkyl is phenylmethyl. In other embodiments, L is C=O, R⁶ is $C_{1-6}$alkyl, Q is selected from O and NH, and R⁷ is $C_{1-6}$heteroaralkyl, where heteroaralkyl is (4-pyridyl)methyl.

In certain embodiments, L is absent or is C=O, and R⁶ and R⁷ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and R⁶ and R⁷ together are $C_{1-3}$alkyl-Y—$C_{1-3}$alkyl. In another preferred embodiment, L and Q are absent, and R⁶ and R⁷ together are $C_{1-3}$alkyl-Y—$C_{1-3}$alkyl. In another preferred embodiment, L is C=O, Q is absent, Y is selected from NH and N—$C_{1-6}$alkyl, and R⁶ and R⁷ together are $C_{1-3}$alkyl-Y—$C_{1-3}$alkyl. In another preferred embodiment, L is C=O, Y is absent, and R⁶ and R⁷ together are $C_{1-3}$alkyl-Y—$C_{1-3}$alkyl. In another preferred embodiment, L and A are C=O, and R⁶ and R⁷ together are $C_{1-2}$alkyl-ZA-$C_{1-2}$alkyl. In another preferred embodiment, L and A are C=O and R⁶ and R⁷ together are $C_{2-3}$alkyl-A.

In certain embodiments, a compound of Formula (2) has the following stereochemistry:

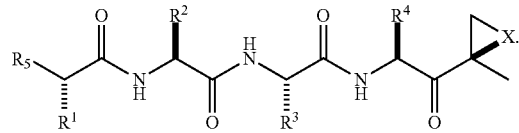

In preferred embodiments, the peptide epoxyketone has a structure of Formula (4) or a pharmaceutically acceptable salt thereof,

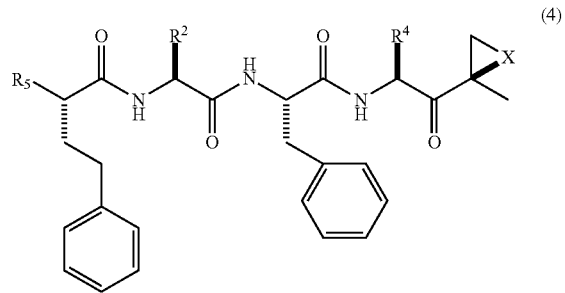

wherein each A is independently selected from C=O, C=S, and SO₂, preferably C=O; or
A is optionally a covalent bond when adjacent to an occurrence of Z;
L is absent or is selected from C=O, C=S, and SO₂, preferably L is absent or C=O;
M is absent or is $C_{1-12}$alkyl, preferably $C_{1-8}$alkyl;
Q is absent or is selected from O, NH, and N—$C_{1-6}$alkyl, preferably Q is absent, O, or NH, most preferably Q is absent or O;
X is O;
Y is absent or is selected from O, NH, N—$C_{1-6}$alkyl, S, SO, SO₂, CHOR¹⁰, and CHCO₂R¹⁰;
each Z is independently selected from O, S, NH, and N—$C_{1-6}$alkyl, preferably O; or
Z is optionally a covalent bond when adjacent to an occurrence of A;
R² and R⁴ are each independently selected from optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, one or more of amide, amine, carboxylic acid (or a salt thereof), ester (including $C_{1-5}$ alkyl ester and aryl ester), thiol, or thioether substituents;
R⁵ is N(R⁶)LQR⁷;
R⁶ is selected from hydrogen, OH, and $C_{1-6}$alkyl, preferably $C_{1-6}$alkyl;
R⁷ is selected from hydrogen, $C_{1-6}$alkyl, $C_{1-6}$alkenyl, $C_{1-6}$alkynyl, aryl, $C_{1-6}$aralkyl, heteroaryl, $C_{1-6}$heteroaralkyl, R⁸ZAZ—$C_{1-8}$alkyl-, R¹¹Z—$C_{1-8}$alkyl-, (R⁸O)(R⁹O)P(=O)O—$C_{1-8}$alkyl-ZAZ—$C_{1-8}$alkyl-, R⁸ZAZ—$C_{1-8}$alkyl-ZAZ—$C_{1-8}$alkyl-, heterocyclylMZAZ—$C_{1-8}$alkyl-, (R⁸O)(R⁹O)P(=O)O—$C_{1-8}$alkyl-, (R¹⁰)₂N—$C_{1-12}$alkyl-, (R¹⁰)₃N⁺—$C_{1-12}$alkyl-, heterocyclylM-, carbocyclylM-, R¹¹SO₂$C_{1-8}$alkyl-, and R¹¹SO₂NH; preferably $C_{1-6}$alkyl, $C_{1-6}$alkenyl, $C_{1-6}$alkynyl, aryl, $C_{1-6}$aralkyl, heteroaryl, $C_{1-6}$heteroaralkyl, R⁸ZA-$C_{1-8}$alkyl-, R¹¹Z—$C_{1-8}$ alkyl-, (R⁸O)(R⁹O)P(=O)O—$C_{1-8}$alkyl-ZAZ—$C_{1-8}$ alkyl-, (R⁸O)(R⁹O)P(=O)O—$C_{1-8}$alkyl-Z—$C_{1-8}$alkyl-, R⁸ZA-$C_{1-8}$alkyl-ZAZ—$C_{1-5}$alkyl-, heterocyclylMZAZ—$C_{1-8}$alkyl-, (R⁸O)(R⁹O)P(=O)O—$C_{1-8}$ alkyl-, (R¹⁰)₂N—$C_{1-8}$alkyl-, (R¹⁰)₃N⁺—$C_{1-8}$ alkyl-, heterocyclylM-, carbocyclylM-, $R^{11}SO_2C_{1-8}$alkyl-, and $R^{11}SO_2NH$, wherein each occurrence of Z and A is independently other than a covalent bond; or $R^6$ and $R^7$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring; preferably $C_{1-2}$alkyl-Y—$C_{1-2}$alkyl, $C_{1-2}$alkyl-ZA-$C_{1-2}$alkyl, A-$C_{1-2}$alkyl-ZA-$C_{1-2}$alkyl, A-$C_{1-3}$alkyl-A, or $C_{1-4}$alkyl-A, wherein each occurrence of Z and A is independently other than a covalent bond;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl; and $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl, provided that when $R^6$ is H or $CH_3$ and Q is absent, $LR^7$ is not hydrogen, unsubstituted $C_{1-6}$alkylC=O, a further chain of amino acids, t-butoxycarbonyl (Boc), benzoyl (Bz), fluoren-9-ylmethoxycarbonyl (Fmoc), triphenylmethyl(trityl), benzyloxycarbonyl (Cbz), trichloroethoxycarbonyl (Troc); or substituted or unsubstituted aryl or heteroaryl; and in any occurrence of the sequence ZAZ, at least one member of the sequence must be other than a covalent bond.

In certain embodiments, L is C=O, Q is absent, $R^6$ is H, and $R^2$ and $R^4$ are selected from $C_{1-6}$alkyl and $C_{1-6}$aralkyl. In preferred such embodiments, $R^2$ and $R^4$ are $C_{1-6}$alkyl. In the most preferred such embodiment, $R^2$ and $R^4$ are isobutyl.

In certain embodiments, L is C=O, Q is absent, $R^6$ is H, $R^2$ and $R^4$ are isobutyl, and $R^7$ is heterocyclylM-, where the heterocycle is a nitrogen-containing heterocycle, such as piperazino (including N-(lower alkyl) piperazino), morpholino, and piperidino. In preferred such embodiments, M is $CH_2$.

Group 3

In certain embodiments, the peptide epoxyketone has a structure of Formula (5) or a pharmaceutically acceptable salt thereof

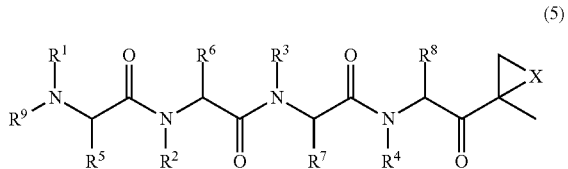

(5)

wherein
X is O;
$R^1$, $R^2$, $R^3$, and $R^4$ are independently selected from hydrogen and a group of Formula (6), with the proviso that at least one of $R^1$, $R^2$, $R^3$, and $R^4$ is a group of Formula (6);

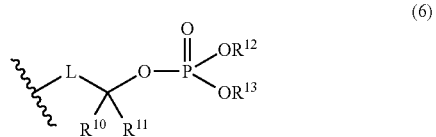

(6)

$R^5$, $R^6$, $R^7$, and $R^8$ are independently selected from optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether;

$R^9$ is a further chain of amino acids, hydrogen, $C_{1-6}$acyl, a protecting group, aryl, or heteroaryl, where substituents may include halogen, carbonyl, nitro, hydroxy, aryl, and $C_{1-5}$alkyl;

$R^{10}$ and $R^{11}$ are independently selected from hydrogen and $C_{1-6}$alkyl, or $R^{10}$ and $R^{11}$ together form a 3- to 6-membered carbocyclic or heterocyclic ring;

$R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; and L is absent or is selected from —$CO_2$ or —C(=S)O.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In some embodiments, any two of $R^1$, $R^2$, $R^3$, and $R^4$ are hydrogen and any two of $R^1$, $R^2$, $R^3$, and $R^4$ have a structure of Formula (6). In preferred embodiments any three of $R^1$, $R^2$, $R^3$, and $R^4$ are hydrogen and any one of $R^1$, $R^2$, $R^3$, and $R^4$ has a structure of Formula (6). In certain preferred embodiments, $R^1$ has a structure of Formula (6) and $R^2$, $R^3$, and $R^4$ are hydrogen.

In certain embodiments, $R^5$, $R^6$, $R^7$, and $R^8$ are $C_{1-6}$alkyl or $C_{1-6}$aralkyl. In preferred embodiments, $R^6$ and $R^8$ are $C_{1-6}$alkyl and $R^5$ and $R^7$ are $C_{1-6}$aralkyl. In the most preferred embodiment, $R^6$ and $R^8$ are isobutyl, $R^5$ is 2-phenylethyl, and $R^7$ is phenylmethyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, a compound of Formula (5) has the following stereochemistry:

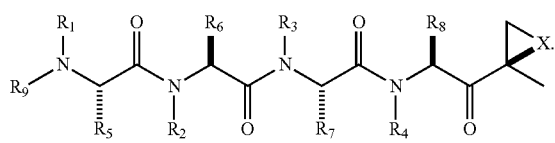

In preferred embodiments, the peptide epoxyketone has a structure of Formula (7) or a pharmaceutically acceptable salt thereof,

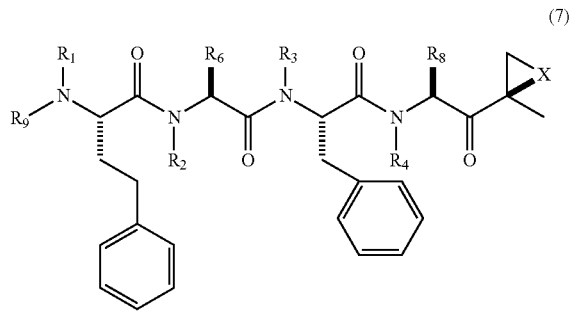

(7)

wherein

X is O;

$R^1$, $R^2$, $R^3$, and $R^4$ are independently selected from hydrogen and a group of Formula (6), with the proviso that at least one of $R^1$, $R^2$, $R^3$, and $R^4$ is a group of Formula (6);

$R^6$ and $R^8$ are independently selected from optionally substituted $C_{1-6}$alkyl, $C_{1-6}$hydroxy alkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether;

$R^9$ is a further chain of amino acids, hydrogen, acyl, a protecting group, aryl, or heteroaryl, where substituents may include halogen, carbonyl, nitro, hydroxy, aryl, and $C_{1-5}$alkyl. Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like; and In some embodiments, any two of $R^1$, $R^2$, $R^3$, and $R^4$ are hydrogen and any two of $R^1$, $R^2$, $R^3$, and $R^4$ have a structure of Formula (6). In preferred embodiments any three of $R^1$, $R^2$, $R^3$, and $R^4$ are hydrogen and any one of $R^1$, $R^2$, $R^3$, and $R^4$ has a structure of Formula (6). In certain preferred embodiments, $R^1$ has a structure of Formula (6) and $R^2$, $R^3$, and $R^4$ are hydrogen.

In certain embodiments, $R^6$ and $R^8$ are $C_{1-6}$alkyl or $C_{1-6}$aralkyl. In preferred embodiments, $R^6$ and $R^8$ are $C_{1-6}$alkyl. In the most preferred embodiment, $R^6$ and $R^8$ are isobutyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, $R^6$ and $R^8$ are $C_{1-6}$alkyl. In preferred embodiments, $R^6$ and $R^8$ are isobutyl. In preferred embodiments, $R^9$ is hydrogen or acetyl. In the most preferred embodiments, $R^9$ is acetyl. In a preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

Group 4

In certain embodiments, the peptide epoxyketone has a structure of Formula (8) or a pharmaceutically acceptable salt thereof,

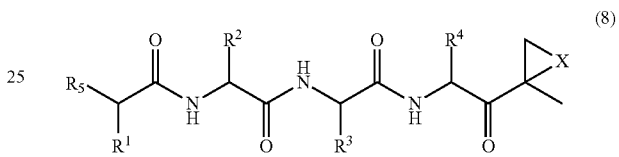

(8)

wherein each A is independently selected from C=O, C=S, and $SO_2$, preferably C=O;

each B is independently selected from C=O, C=S, and $SO_2$, preferably C=O;

D is absent or is $C_{1-8}$alkyl;

G is selected from O, NH, and N—$C_{1-6}$alkyl;

K is absent or is selected from C=O, C=S, and $SO_2$, preferably K is absent or is C=O;

L is absent or is selected from C=O, C=S, and $SO_2$, preferably L is absent or C=O;

M is absent or is $C_{1-8}$alkyl;

Q is absent or is selected from O, NH, and N—$C_{1-6}$alkyl, preferably Q is absent, O, or NH, most preferably Q is absent;

X is O;

each V is independently absent or is selected from O, S, NH, and N—$C_{1-6}$alkyl, preferably V is absent or O;

W is absent or is independently selected from O, S, NH, and N—$C_{1-6}$alkyl, preferably O;

Y is absent or is selected from O, NH, N—$C_{1-6}$alkyl, S, SO, $SO_2$, $CHOR^{10}$, and $CHCO_2R^{10}$;

each Z is independently selected from O, S, NH, and N—$C_{1-6}$alkyl, preferably O;

$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl-, wherein at least one of $R^1$ and $R^3$ is $R^{14}DVKOC_{1-3}$alkyl-;

$R^5$ is $N(R^6)LQR^7$;

$R^6$ is selected from hydrogen, OH, and $C_{1-6}$alkyl, preferably $C_{1-6}$alkyl;

$R^7$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^7$ is selected from $C_{1-6}$alkyl, $C_{1-6}$alkenyl, $C_{1-6}$alkynyl, $C_{1-6}$aralkyl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-ZAZ—$C_{1-6}$alkyl-, $(R^8O)(R^9O)P(=O)O$ —$C_{1-8}$alkyl-Z—$C_{1-8}$alkyl-, $R^8$ZA-$C_{1-8}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^1SO_2NH$—; or $R^6$ and $R^7$ together are $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, preferably $C_{1-2}$alkyl-Y—$C_{1-2}$alkyl, $C_{1-2}$alkyl-ZA-$C_{1-2}$alkyl, A-$C_{1-2}$alkyl-ZA-$C_{1-2}$alkyl, A-$C_{1-3}$alkyl-A, or $C_{1-4}$alkyl-A, thereby forming a ring, preferably $R^6$ is hydrogen and $R^7$ is $C_{1-6}$alkyl;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl;

each $R^{11}$ is independently selected from hydrogen, $OR^{10}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{14}$ is selected from hydrogen, $(R^{15}O)(R^{16}O)P(=O)W$—, $R^{15}GB$—, heterocyclyl-, $(R^{17})_2N$—, $(R^{17})_3N^+$—, $R^{17}SO_2GBG$-, and $R^{15}GBC_{1-8}$alkyl- where the $C_{1-8}$alkyl moiety is optionally substituted with OH, $C_{1-8}$alkylW (optionally substituted with halogen, preferably fluorine), aryl, heteroaryl, carbocyclyl, heterocyclyl, and $C_{1-6}$aralkyl, preferably at least one occurrence of $R^{14}$ is other than hydrogen;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{15}$ and $R^{16}$ together are $C_{1-6}$alkyl, thereby forming a ring; and each $R^{17}$ is independently selected from hydrogen, $OR^{10}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or substituted or unsubstituted aryl or heteroaryl; and D, G, V, K, and W are selected such that there are no O—O, N—O, S—N, or S—O bonds.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In certain embodiments, $R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl- wherein at least one of $R^1$ and $R^3$ is $R^{14}DVKOC_{1-3}$alkyl-. In preferred embodiments, one of $R^1$ and $R^3$ is $C_{1-6}$aralkyl and the other is $R^{14}DVKOC_{1-3}$alkyl-, and $R^2$ and $R^4$ are independently $C_{1-6}$alkyl. In the most preferred embodiment, one of $R^1$ and $R^3$ is 2-phenylethyl or phenylmethyl and the other is $R^{14}DVKOCH_2$— or $R^{14}DVKO(CH_3)CH$—, and both $R^2$ and $R^4$ are isobutyl.

In certain embodiments, each $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, each $R^{17}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, L and Q are absent and $R^7$ is selected from hydrogen, a further chain of amino acids, $C_{1-6}$acyl, a protecting group, aryl, heteroaryl, $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8$ZA-$C_{1-8}$alkyl-, $R^{11}Z$—$C_{1-8}$alkyl-, $(R^8O)(R^9O)P(=O)O$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8$ZA-$C_{1-8}$alkyl-ZAZ—$C_{1-8}$alkyl-, heterocyclylMZAZ—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$—. In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methylsulfonyl)ethyl.

In other embodiments, L is C=O, Q is absent, and $R^7$ is $C_{1-6}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is substituted or unsubstituted phenyl.

In certain embodiments, L is C=O, Q is absent or O, and $R^7$ is —$(CH_2)_n$carbocyclyl. In certain such embodiments, $R^7$ is cyclopropyl or cyclohexyl.

In certain embodiments, L and A are C=O, Q is absent, Z is O, and $R^7$ is selected from $R^8$ZA-$C_{1-8}$alkyl-, $R^{11}Z$—$C_{1-8}$alkyl-, $R^8$ZA-$C_{1-8}$alkyl-ZAZ—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, and heterocyclylMZAZ—$C_{1-8}$alkyl-. In certain such embodiments, $R^7$ is heterocyclylMZAZ—$C_{1-8}$alkyl- where heterocyclyl is substituted or unsubstituted oxodioxolenyl or $N(R^{12})(R^{13})$, wherein $R^{12}$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, and $R^7$ is selected from $(R^8O)(R^9O)P(=O)O$—$C_{1-8}$alkyl-, $(R^{10})_2NC_{1-8}$alkyl, $(R^{10})_3N^+(CH_2)_n$—, and heterocyclyl-M-. In certain such embodiments, $R^7$ is —$C_{1-8}$alkylN$(R^{10})_2$ or —$C_{1-8}$alkylN$^+(R^{10})_3$, where $R^{10}$ is $C_{1-6}$alkyl. In certain other such embodiments, $R^7$ is heterocyclylM-, where heterocyclyl is selected from morpholino, piperidino, piperazino, and pyrrolidino.

In certain embodiments, L is C=O, $R^6$ is $C_{1-6}$alkyl, Q is selected from O and NH and $R^7$ is selected from $C_{1-6}$alkyl, cycloalkyl-M, $C_{1-6}$aralkyl, and $C_{1-6}$heteroaralkyl. In other embodiments, L is C=O, $R^6$ is $C_{1-6}$alkyl, Q is selected from O and NH, and $R^7$ is $C_{1-6}$alkyl, where $C_{1-6}$alkyl is selected from methyl, ethyl, and isopropyl. In further embodiments, L is C=O, $R^6$ is $C_{1-6}$alkyl, Q is selected from O and NH and $R^7$ is $C_{1-6}$aralkyl, where aralkyl is phenylmethyl. In other embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In certain embodiments, L is absent or is C=O, and $R^6$ and $R^7$ together are $C_{1-6}$alkyl-Y—$C_{1-6}$alkyl, $C_{1-6}$alkyl-ZA-$C_{1-6}$alkyl, or $C_{1-6}$alkyl-A, thereby forming a ring. In certain preferred embodiments, L is C=O, Q and Y are absent, and $R^6$ and $R^7$ together are $C_{1-3}$alkyl-Y—$C_{1-3}$alkyl. In another preferred embodiment, L and Q are absent, and $R^6$ and $R^7$ together are $C_{1-3}$alkyl-Y—$C_{1-3}$alkyl. In another preferred embodiment, L is C=O, Q is absent, Y is selected from NH and N—$C_{1-6}$alkyl, and $R^6$ and $R^7$ together are $C_{1-3}$alkyl-Y—$C_{1-3}$alkyl. In another preferred embodiment, L is C=O, Y is absent, and $R^6$ and $R^7$ together are $C_{1-3}$alkyl-Y—$C_{1-3}$alkyl. In another preferred embodiment, L and A are C=O, and $R^6$ and $R^7$ together are $C_{1-2}$alkyl-ZA-$C_{1-2}$alkyl. In another preferred embodiment, L and A are C=O and $R^6$ and $R^7$ together are $C_{2-3}$alkyl-A.

In certain embodiments, $R^{14}$ is $(R^{15}O)(R^{16}O)P(=O)W—$. In certain such embodiments, D, V, K, and W are absent. In other such embodiments, V and K are absent, D is $C_{1-8}$alkyl, and W is O. In yet other such embodiments, D is $C_{1-8}$alkyl, K is C=O, and V and W are O.

In certain embodiments, $R^{14}$ is $R^{15}GB—$. In preferred embodiments, B is C=O, G is O, D is $C_{1-8}$alkyl, V is O, and K is C=O.

In certain embodiments, $R^{14}$ is heterocyclyl-. In preferred such embodiments, D is $C_{1-8}$alkyl. In certain such embodiments, V is O, K is C=O, and heterocyclyl is oxodioxolenyl. In other such embodiments, V is absent, K is absent or is C=O, and heterocyclyl is $N(R^{18})(R^{19})$, where $R^{18}$ and $R^{19}$ together are J-T-J, J-WB-J, or B-J-T-J, T is absent or is selected from O, $NR^{17}$, S, SO, $SO_2$, $CHOR^{17}$, $CHCO_2R^{15}$, C=O, $CF_2$, and CHF, and J is absent or is $C_{1-3}$alkyl.

In certain embodiments, $R^{14}$ is $(R^{17})_2N—$ or $(R^{17})_3N^+—$, and preferably V is absent. In preferred such embodiments, D is $C_{1-8}$alkyl and K is absent or C=O. In certain embodiments where V is absent and $R^{14}$ is $(R^{17})_2N—$, D is absent K is absent or is C=O, preferably K is C=O.

In certain embodiments, $R^{14}$ is $R^{17}SO_2GBG$-. In preferred such embodiments, B is C=O, D, V, and K are absent, and G is NH or $NC_{1-6}$alkyl.

In certain embodiments, $R^{14}$ is $R^{15}GBC_{1-8}$alkyl-. In preferred embodiments, B is C=O, G is O, and the $C_{1-8}$alkyl moiety is optionally substituted with OH, $C_{1-8}$alkyl (optionally substituted with halogen, preferably fluorine), $C_{1-8}$alkylW, aryl, heteroaryl, carbocyclyl, heterocyclyl, and $C_{1-6}$aralkyl. In certain such embodiments, the $C_{1-8}$alkyl moiety is an unsubstituted, mono-, or disubstituted $C_1$alkyl.

In certain embodiments, a compound of Formula (8) has the following stereochemistry:

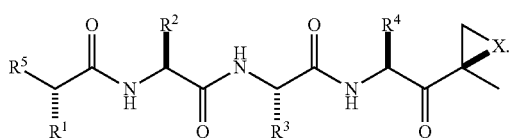

In certain preferred embodiments, the peptide epoxyketone has a structure of Formula (9) or a pharmaceutically acceptable salt thereof,

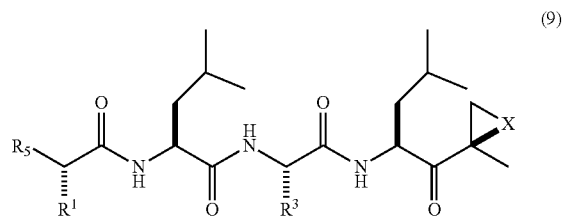

wherein
each A is independently selected from C=O, C=S, and $SO_2$, preferably C=O;
each B is independently selected from C=O, C=S, and $SO_2$, preferably C=O;
D is absent or is $C_{1-8}$alkyl;
G is selected from O, NH, and N—$C_{1-6}$alkyl;
K is absent or is selected from C=O, C=S, and $SO_2$, preferably K is absent or is C=O;
L is absent or is selected from C=O, C=S, and $SO_2$, preferably L is absent or C=O;
M is absent or is $C_{1-8}$alkyl;
Q is absent or is selected from O, NH, and N—$C_{1-6}$alkyl, preferably Q is absent, O, or NH, most preferably Q is absent or O;
X is O;
each V is independently absent or is selected from O, S, NH, and N—$C_{1-6}$alkyl, preferably V is absent or O;
W is absent or is independently selected from O, S, NH, and N—$C_{1-6}$alkyl, preferably O;
Y is absent or is selected from O, NH, N—$C_{1-6}$alkyl, S, SO, $SO_2$, $CHOR^{10}$, and $CHCO_2R^{10}$;
each Z is independently selected from O, S, NH, and N—$C_{1-6}$alkyl, preferably O;
$R^1$ and $R^3$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl-, wherein at least one of $R^1$ and $R^3$ is $R^{14}DVKOC_{1-3}$alkyl-;
$R^5$ is $N(R^6)LQR^7$;
$R^6$ is selected from hydrogen, OH, and $C_{1-6}$alkyl, preferably $C_{1-6}$alkyl;
$R^7$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^7$ is selected from $C_{1-6}$alkyl, $C_{1-6}$alkenyl, $C_{1-6}$alkynyl, $C_{1-6}$aralkyl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-5}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$; or
$R^6$ and $R^7$ together are $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, preferably $C_{1-2}$alkyl-Y—$C_{1-2}$alkyl, $C_{1-2}$alkyl-ZA-$C_{1-2}$alkyl, A-$C_{1-2}$alkyl-ZA-$C_{1-2}$alkyl, A-$C_{1-3}$alkyl-A, or $C_{1-4}$alkyl-A, thereby forming a ring;
$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl; and each $R^{11}$ is independently selected from hydrogen, $OR^{10}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{14}$ is selected from hydrogen, $(R^{15}O)(R^{16}O)P(=O)W-$, $R^{15}GB-$, heterocyclyl-, $(R^{17})_2N-$, $(R^{17})_3N^+-$, $R^{17}SO_2GBG-$, and $R^{15}GBC_{1-8}$alkyl- where the $C_{1-8}$alkyl moiety is optionally substituted with OH, $C_{1-8}$alkylW (optionally substituted with halogen, preferably fluorine), aryl, heteroaryl, carbocyclyl, heterocyclyl, and $C_{1-6}$aralkyl, preferably at least one occurrence of $R^{14}$ is other than hydrogen;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{15}$ and $R^{16}$ together are $C_{1-6}$alkyl, thereby forming a ring;

each $R^{17}$ is independently selected from hydrogen, $OR^{10}$, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or substituted or unsubstituted aryl or heteroaryl; and D, G, V, K, and W are selected such that there are no O—O, N—O, S—N, or S—O bonds.

In certain embodiments, $R^1$ and $R^3$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl- wherein at least one of $R^1$ and $R^3$ is $R^{14}DVKOC_{1-3}$alkyl-. In preferred embodiments, one of $R^1$ and $R^3$ is $C_{1-6}$aralkyl and the other is $R^{14}DVKOC_{1-3}$alkyl-. In the most preferred embodiment, one of $R^1$ and $R^3$ is 2-phenylethyl or phenylmethyl and the other is $R^{14}DVKOCH_2-$ or $R^{14}DVKO(CH_3)CH-$.

In certain embodiments, each $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, each $R^{17}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, L and Q are absent and $R^7$ is selected from hydrogen, a further chain of amino acids, $C_{1-6}$acyl, a protecting group, aryl, heteroaryl, $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA-C_{1-8}$alkyl-, $R^{11}Z-C_{1-8}$alkyl-, $(R^8O)(R^9O)P(=O)O-C_{1-8}$alkyl-, $(R^8O)(R^9O)P(=O)O-C_{1-8}$alkyl-ZAZ—$C_{1-8}$alkyl-, $(R^8O)(R^9O)P(=O)O-C_{1-8}$alkyl-Z—$C_{1-8}$alkyl-, $R^8ZA-C_{1-8}$alkyl-ZAZ—$C_{1-8}$alkyl, heterocyclylMZAZ—$C_{1-8}$alkyl-, $(R^{10})_2N-C_{1-8}$alkyl-, $(R^{10})_3N^+-C_{1-8}$alkyl-, heterocyclylM-, carbocyclylM-, $R^{11}SO_2C_{1-8}$alkyl-, and $R^{11}SO_2NH-$. In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methyl sulfonyl)ethyl.

In other embodiments, L is C=O, Q is absent, and $R^7$ is $C_{1-6}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is substituted or unsubstituted phenyl.

In certain embodiments, L is C=O, Q is absent or O, and $R^7$ is $—(CH_2)_n$carbocyclyl. In certain such embodiments, $R^7$ is cyclopropyl or cyclohexyl.

In certain embodiments, L and A are C=O, Q is absent, Z is O, and $R^7$ is selected from $R^8ZA-C_1$ alkyl-, $R^{11}Z—C_{1-8}$ alkyl-, $R^8ZA-C_{1-8}$alkyl-ZAZ—$C_{1-8}$alkyl-, $(R^8O)(R^9O)P(=O)O-C_{1-8}$alkyl-ZAZ—$C_{1-8}$alkyl-, $(R^8O)(R^9O)P(=O)O-C_{1-8}$alkyl-Z—$C_{1-8}$alkyl-, and heterocyclylMZAZ—$C_{1-8}$alkyl-. In certain such embodiments, $R^7$ is heterocyclylMZAZ—$C_{1-8}$alkyl- where heterocyclyl is substituted or unsubstituted oxodioxolenyl or $N(R^{12})(R^{13})$, wherein $R^2$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, and $R^7$ is selected from $(R^8O)(R^9O)P(=O)O-C_{1-8}$alkyl-, $(R^{10})_2NC_{1-8}$alkyl, $(R^{10})_3N^+(CH_2)_n-$, and heterocyclyl-M-. In certain such embodiments, $R^7$ is $-C_{1-8}$alkylN($R^{10})_2$ or $-C_{1-8}$alkylN$^+(R^{10})_3$, where $R^{10}$ is $C_{1-6}$alkyl. In certain other such embodiments, $R^7$ is heterocyclylM-, where heterocyclyl is selected from morpholino, piperidino, piperazino, and pyrrolidino.

In certain embodiments, L is C=O, $R^6$ is $C_{1-6}$alkyl, Q is selected from O and NH and $R^7$ is selected from $C_{1-6}$alkyl, cycloalkyl-M, $C_{1-6}$araalkyl, and $C_{1-6}$heteroaralkyl. In other embodiments, L is C=O, $R^6$ is $C_{1-6}$alkyl, Q is selected from O and NH, and $R^7$ is $C_{1-6}$alkyl, where $C_{1-6}$alkyl is selected from methyl, ethyl, and isopropyl. In further embodiments, L is C=O, $R^6$ is $C_{1-6}$alkyl, Q is selected from O and NH and $R^7$ is $C_{1-6}$aralkyl, where aralkyl is phenylmethyl. In other embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In certain embodiments, L is absent or is C=O, and $R^6$ and $R^7$ together are $C_{1-6}$alkyl-Y—$C_{1-6}$alkyl, $C_{1-6}$alkyl-ZA-$C_{1-6}$alkyl, or $C_{1-6}$alkyl-A, thereby forming a ring. In certain preferred embodiments, L is C=O, Q and Y are absent, and $R^6$ and $R^7$ together are $C_{1-3}$alkyl-Y—$C_{1-3}$alkyl. In another preferred embodiment, L and Q are absent, and $R^6$ and $R^7$ together are $C_{1-3}$alkyl-Y—$C_{1-3}$alkyl. In another preferred embodiment, L is C=O, Q is absent, Y is selected from NH and N—$C_{1-6}$alkyl, and $R^6$ and $R^7$ together are $C_{1-3}$alkyl-Y—$C_{1-3}$alkyl. In another preferred embodiment, L is C=O, Y is absent, and $R^6$ and $R^7$ together are $C_{1-3}$alkyl-Y—$C_{1-3}$alkyl. In another preferred embodiment, L and A are C=O, and $R^6$ and $R^7$ together are $C_{1-2}$alkyl-ZA-$C_{1-2}$alkyl. In another preferred embodiment, L and A are C=O and $R^6$ and $R^7$ together are $C_{2-3}$alkyl-A.

In certain embodiments, $R^{14}$ is $(R^{15}O)(R^{16}O)P(=O)W-$. In certain such embodiments, D, V, K, and W are absent. In other such embodiments, V and K are absent, D is $C_{1-8}$alkyl, and W is O. In yet other such embodiments, D is $C_{1-8}$alkyl, K is C=O, and V and W are O.

In certain embodiments, $R^{14}$ is $R^{15}GB-$. In preferred embodiments, B is C=O, G is O, D is $C_{1-8}$alkyl, V is O, and K is C=O.

In certain embodiments, $R^{14}$ is heterocyclyl-. In preferred such embodiments, D is $C_{1-8}$alkyl. In certain such embodiments, V is O, K is C=O, and heterocyclyl is oxodioxolenyl. In other such embodiments, V is absent, K is absent or is C=O, and heterocyclyl is $N(R^{18})(R^{19})$, where $R^{18}$ and $R^{19}$ together are J-T-J, J-WB-J, or B-J-T-J, T is absent or is selected from O, $NR^{17}$, S, SO, $SO_2$, $CHOR^{17}$, $CHCO_2R^{15}$, C=O, $CF_2$, and CHF, and J is absent or is $C_{1-3}$alkyl.

In certain embodiments, $R^{14}$ is $(R^{17})_2N-$ or $(R^{17})_3N^+-$, and preferably V is absent. In preferred such embodiments, D is $C_{1-8}$alkyl and K is absent or C=O. In certain embodiments where V is absent and $R^{14}$ is $(R^{17})_2N-$, D is absent K is absent or is C=O, preferably K is C=O.

In certain embodiments, $R^{14}$ is $R^{17}SO_2GBG-$. In preferred such embodiments, B is C=O, D, V, and K are absent, and G is NH or $NC_{1-6}$alkyl.

In certain embodiments, $R^{14}$ is $R^{15}GBC_{1-8}$alkyl-. In preferred embodiments, B is C=O, G is O, and the $C_{1-8}$alkyl moiety is optionally substituted with OH, $C_{1-8}$alkyl (optionally substituted with halogen, preferably fluorine), $C_{1-8}$alkylW, aryl, heteroaryl, carbocyclyl, heterocyclyl, and $C_{1-6}$aralkyl. In certain such embodiments, the $C_{1-8}$alkyl moiety is an unsubstituted, mono-, or disubstituted $C_1$alkyl.

Group 5

In certain embodiments, the peptide epoxyketone has a structure of Formula (10) or a pharmaceutically acceptable salt thereof,

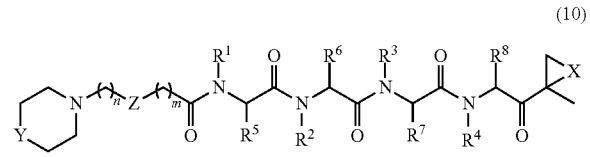

(10)

wherein

L is absent or is selected from $-CO_2$ or $-C(=S)O$;

X is O;

Y is NH, N-alkyl, O, or $C(R^9)_2$, preferably N-alkyl, O, or $C(R^9)_2$;

Z is O or $C(R^9)_2$, preferably $C(R^9)_2$;

$R^1$, $R^2$, $R^3$, and $R^4$ are independently selected from hydrogen and a group of Formula (11), preferably, $R^1$, $R^2$, $R^3$, and $R^4$ are all the same, more preferably $R^1$, $R^2$, $R^3$, and $R^4$ are all hydrogen;

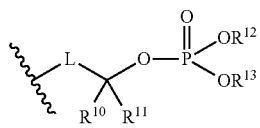

(11)

each $R^5$, $R^6$, $R^7$, $R^8$, and $R^9$ is independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, alkyl, amide, amine, carboxylic acid or a pharmaceutically acceptable salt thereof, carboxyl ester, thiol, and thioether, preferably $R^5$, $R^6$, $R^7$, and $R^8$ are independently selected from $C_{1-6}$alkyl, $C_{1-6}$hydroxyalkyl, and $C_{1-6}$aralkyl and each $R^9$ is hydrogen, more preferably, $R^6$ and $R^8$ are independently $C_{1-6}$alkyl, $R^5$ and $R^7$ are independently $C_{1-6}$aralkyl and each $R^9$ is H;

$R^{10}$ and $R^{11}$ are independently selected from hydrogen and $C_{1-6}$alkyl, or $R^{10}$ and $R^{11}$ together form a 3- to 6-membered carbocyclic or heterocyclic ring;

$R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring;

m is an integer from 0 to 2; and n is an integer from 0 to 2, preferably 0 or 1.

In certain embodiments, $R^1$, $R^2$, $R^3$, and $R^4$ are all the same, preferably $R^1$, $R^2$, $R^3$, and $R^4$ are all hydrogen. In certain such embodiments, $R^5$, $R^6$, $R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl.

In certain preferred embodiments, $R^1$, $R^2$, $R^3$, and $R^4$ are all hydrogen, $R^6$ and $R^8$ are both isobutyl, $R^5$ is phenylethyl, and $R^7$ is phenylmethyl.

In certain embodiments, $R^5$, $R^6$, $R^7$, and $R^8$ are independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, alkyl, amide, amine, carboxylic acid or a pharmaceutically acceptable salt thereof, carboxyl ester, thiol, and thioether. In certain embodiments, at least one of $R^5$ and $R^7$ is $C_{1-6}$aralkyl substituted with alkyl, more preferably substituted with perhaloalkyl. In certain such embodiments, $R^7$ is $C_{1-6}$aralkyl substituted with trifluoromethyl.

In certain embodiments, Y is selected from N-alkyl, O, and $CH_2$. In certain such embodiments, Z is $CH_2$, and m and n are both 0. In certain alternative such embodiments, Z is $CH_2$, m is 0, and n is 2 or 3. In yet another alternative such embodiments, Z is O, m is 1, and n is 2.

Group 6

In certain embodiments, the peptide epoxyketone has a structure of Formula (12) or a pharmaceutically acceptable salt thereof,

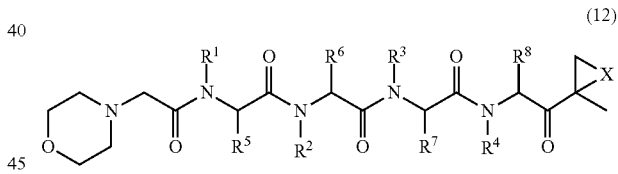

(12)

where X is O;

$R^1$, $R^2$, $R^3$, and $R^4$ are independently selected from hydrogen and a group of Formula (11), preferably, $R^1$, $R^2$, $R^3$, and $R^4$ are all the same, more preferably $R^1$, $R^2$, $R^3$, and $R^4$ are all hydrogen; and $R^5$, $R^6$, $R^7$, and $R^8$ are independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether, preferably $R^5$, $R^6$, $R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl.

In certain embodiments, $R^1$, $R^2$, $R^3$, and $R^4$ are all the same, preferably $R^1$, $R^2$, $R^3$, and $R^4$ are all hydrogen. In certain such embodiments, $R^5$, $R^6$, $R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl.

In certain preferred embodiments, $R^1$, $R^2$, $R^3$, and $R^4$ are all hydrogen, $R^6$ and $R^8$ are both isobutyl, $R^5$ is phenylethyl, and $R^7$ is phenylmethyl.

In certain embodiments, a compound of Formula (12) has the following stereochemistry:

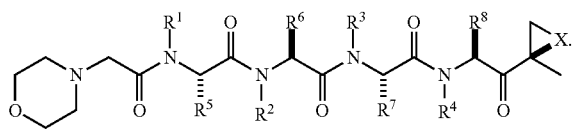

In certain preferred embodiments, the peptide epoxyketone has a structure of Formula (13) or a pharmaceutically acceptable salt thereof,

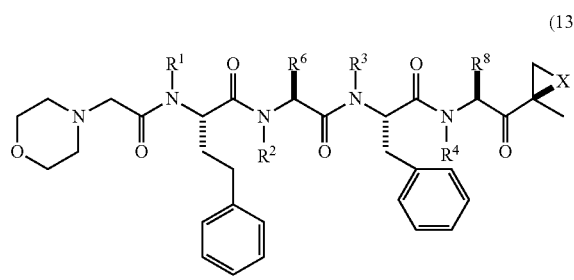

wherein

X is O;

$R^1$, $R^2$, $R^3$, and $R^4$ are independently selected from hydrogen and a group of Formula (11), preferably, $R^1$, $R^2$, $R^3$, and $R^4$ are all the same, more preferably $R^1$, $R^2$, $R^3$, and $R^4$ are all hydrogen; and $R^6$ and $R^8$ are independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether, preferably $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl.

In certain embodiments, $R^1$, $R^2$, $R^3$, and $R^4$ are all the same, preferably $R^1$, $R^2$, $R^3$, and $R^4$ are all hydrogen. In certain such embodiments, $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl.

In certain preferred embodiments, $R^1$, $R^2$, $R^3$, and $R^4$ are all hydrogen, and $R^6$ and $R^8$ are both isobutyl.

In certain embodiments, a compound of Formula (13) has the following structure:

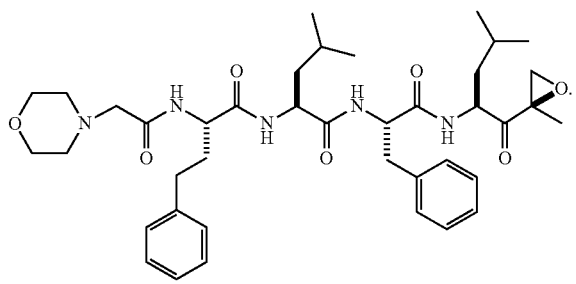

Compound 1

Group 7

In certain embodiments, the peptide epoxyketone has a structure of Formula (14) or a pharmaceutically acceptable salt thereof

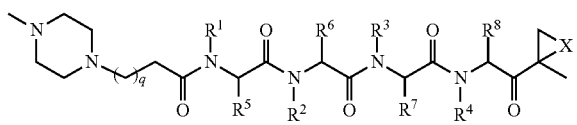

(14)

wherein

X is O;

$R^1$, $R^2$, $R^3$, and $R^4$ are independently selected from hydrogen and a group of formula II, preferably, $R^1$, $R^2$, $R^3$, and $R^4$ are all the same, more preferably $R^1$, $R^2$, $R^3$, and $R^4$ are all hydrogen;

$R^5$, $R^6$, $R^7$, and $R^8$ are independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether, preferably $R^5$, $R^6$, $R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl; and q is an integer from 0 to 3.

In certain preferred embodiments, the peptide epoxyketone has a structure of Formula (15) or a pharmaceutically acceptable salt thereof,

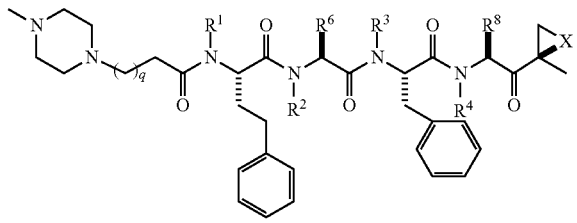

(15)

wherein

X is O;

$R^1$, $R^2$, $R^3$, and $R^4$ are independently selected from hydrogen and a group of Formula (15), preferably, $R^1$, $R^2$, $R^3$, and $R^4$ are all the same, more preferably $R^1$, $R^2$, $R^3$, and $R^4$ are all hydrogen;

$R^6$ and $R^8$ are independently selected from hydrogen and optionally substituted $C_{1-6}$alkyl, $C_{1-6}$hydroxyalkyl, $C_{1-6}$alkoxyalkyl, aryl, and $C_{1-6}$aralkyl, wherein substituents may include, but are not limited to, amide, amine, carboxylic acid or a pharmaceutically acceptable salt thereof, carboxyl ester, thiol, and thioether, preferably $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl; and q is an integer from 0 to 3.

In certain embodiments, $R^1$, $R^2$, $R^3$, and $R^4$ are all the same, preferably $R^1$, $R^2$, $R^3$, and $R^4$ are all hydrogen. In certain such embodiments, $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl.

In certain preferred embodiments, $R^1$, $R^2$, $R^3$, and $R^4$ are all hydrogen, and $R^6$ and $R^8$ are both isobutyl.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

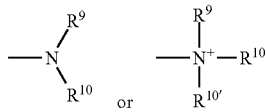

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$ and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as an amino-substituted carbonyl and includes a moiety that can be represented by the general formula:

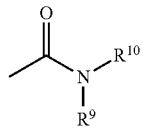

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

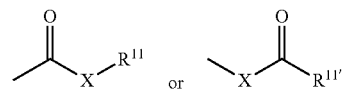

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{1'}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "$C_{1-6}$heteroaralkyl", as used herein, refers to a $C_{1-6}$alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, piperidine, piperazine, pyrrolidine, morpholine, lactones, lactams, and the like.

The term "$C_{1-6}$heterocycloalkyl", as used herein, refers to a $C_{1-6}$alkyl group substituted with a heterocyclyl group.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Combination Therapy

In certain embodiments, the other therapeutic agent is an HDAC inhibitor (e.g., Trichostatin A, depsipeptide, apicidin, A-161906, scriptaid, PXD-101, CHAP, butyric acid, depudecin, oxamflatin, phenylbutyrate, valproic acid, SAHA (Vorinostat), MS275 (N-(2-Aminophenyl)-4-[N-(pyridine-3-ylmethoxy-carbonyl)aminomethyl]benzamide), LAQ824/LBH589, CI994, and MGCD0103). In certain such embodiments, the other agent is SAHA (suberoylanilide hydroxamic acid).

In certain embodiments, the other therapeutic agent is an antibiotic (e.g., dactinomycin (actinomycin D), daunorubicin, doxorubicin and idarubicin). In certain such embodiments, the other therapeutic agent comprises doxorubicin. In certain such embodiments, the other therapeutic agent is Doxil.

In certain embodiments, the other therapeutic agent is a taxane (e.g., paclitaxel and docetaxel).

In certain embodiments, the other therapeutic agent is an antiproliferative/antimitotic alkylating agents such as a nitrogen mustard (e.g., mechlorethamine, ifosphamide, cyclophosphamide and analogs, melphalan, and chlorambucil). In certain such embodiments, the other therapeutic agent is cyclophosphamide or melphalan.

In certain embodiments, the other therapeutic agent is a platinum coordination complex (e.g., cisplatin and carboplatin). In certain such embodiments, the other therapeutic agent is carboplatin.

In certain embodiments, the other therapeutic agent is a steroid (e.g., hydrocortisone, dexamethasone, methylprednisolone and prednisolone). In certain such embodiments, the other therapeutic agent is dexamethasone.

In certain embodiments, the other therapeutic agent is an immunomodulator (e.g., thalidomide, CC-4047 (Actimid), and lenalidomide (Revlimid). In certain such embodiments, the other therapeutic agent is lenalidomide.

In certain embodiments, the other therapeutic agent is a topoisomerase inhibitor (e.g., irinotecan, topotecan, camptothecin, lamellarin D, and etoposide).

In certain embodiments, the other therapeutic agent is an m-TOR inhibitor (e.g., CCI-779, AP23573 and RAD-001).

In certain embodiments, the other therapeutic agent is a protein kinase inhibitor (e.g., sorafenib, imatinib, dasatinib, sunitinib, pazopanib, and nilotinib). In certain such embodiments, the protein kinase inhibitor is sorafenib.

Administration of the peptide epoxyketone may precede or follow the other therapeutic agent by intervals ranging from minutes to days. In certain such embodiments, the peptide epoxyketone and the other therapeutic agent may be administered within about 1 minute, about 5 minutes, about 10 minutes, about 30 minutes, about 60 minutes, about 2 hours, about 4 hours, about 6 hours, 8 hours, about 10 hours, about 12 hours, about 18 hours, about 24 hours, about 36 hours, or even about 48 hours or more of one another. Preferably, administration of the peptide epoxyketone and the other therapeutic agent will be within about 1 minute, about 5 minutes, about 30 minutes, or even about 60 minutes of one another.

In certain embodiments, the peptide epoxyketone and the other therapeutic agent may be administered according to different dosing schedules (e.g., the peptide epoxyketone, for example may be administered once a day while the other therapeutic agent may be administered only once every three weeks) such that in some instances administration of the peptide epoxyketone and the other therapeutic agent will be within about 60 minutes of one another, while in other instances, administration of the peptide epoxyketone and the other therapeutic agent will be within days or even weeks of one another.

As used herein, the term "regimen" is a predetermined schedule of one or more therapeutic agents for the treatment of a cancer. Accordingly, when a therapeutic agent is administered "alone," the regimen does not include the use of another therapeutic agent for the treatment of cancer.

In certain embodiments, combinations as described herein may be synergistic in nature, meaning that the therapeutic effect of the combination of the peptide epoxyketone and the other therapeutic agent(s) is greater than the sum of the individual effects.

In certain embodiments, combinations as described herein may be additive in nature, meaning that the therapeutic effect of the combination of the peptide epoxyketone and the other therapeutic agent(s) is greater than the effect of each agent individually (i.e., the therapeutic effect is the sum of the individual effects).

Compounds described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), or drop infusion preparations. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. The dosage will vary depending on the symptoms, age and body weight of the patient, the nature and severity of the disorder to be treated or prevented, the route of administration and the form of the drug. The amount of active ingredient which can be combined with a carrier material to produce a single dosage form will generally be that amount of the compound which produces a therapeutic effect.

In one embodiment, the present invention is a pharmaceutical composition that includes a practically insoluble proteasome inhibitor, a cyclodextrin and optionally a buffer. Such pharmaceutical compositions typically include a pharmaceutically effective amount of the proteasome inhibitor, e.g., which ameliorates the effects of cancer, when administered to a patient.

In certain embodiments, the peptide epoxyketone and the other therapeutic agent may be in the same form (e.g., both may be administered as tablets or both may be administered intravenously) while in certain alternative embodiments, the peptide epoxyketone and the other therapeutic agent may be in different forms (e.g. one may be administered as a tablet while the other is administered intravenously).

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The following examples are presented in order to more fully illustrate the preferred embodiments of the invention.

These examples should in no way be construed as limiting the scope of the invention, as defined by the appended claims.

Uses of Compounds

Orderly protein degradation is crucial to the maintenance of normal cell functions, and the proteasome is integral to the protein degradation process. The proteasome controls the levels of proteins that are important for cell-cycle progression and apoptosis in normal and malignant cells; for example, cyclins, caspases, BCL2 and nF-kB (Kumatori et al., Proc. Natl. Acad. Sci. USA (1990) 87:7071-7075; Almond et al., Leukemia (2002) 16: 433-443). Thus, it is not surprising that inhibiting proteasome activity can translate into therapies to treat various disease states, such as malignant, non-malignant and autoimmune diseases, depending on the cells involved.

Chemotherapeutic agents are drugs that are used in the treatment of diseases where killing the aberrant cell is warranted, such as autoimmune diseases, like multiple sclerosis and rheumatoid arthritis, and cancer. Although the mechanism by which each category of chemotherapeutic agent may differ, they generally function by disrupting a cell's ability to proliferate.

In accordance with the invention, a peptide epoxyketone or a pharmaceutically acceptable salt thereof in combination with one or more other therapeutic agents can be used in the treatment of a wide variety of cancers and auto-immune diseases.

As used herein, the term "cancer" includes, but is not limited to, blood born and solid tumors. Cancer refers to disease of blood, bone, organs, skin tissue and the vascular system, including, but not limited to, cancers of the bladder, blood, bone, brain, breast, cervix, chest, colon, endrometrium, esophagus, eye, head, kidney, liver, lung, lymph nodes, mouth, neck, ovaries, pancreas, prostate, rectum, renal, skin, stomach, testis, throat, and uterus. Specific cancers include, but are not limited to, leukemia (acute lymphocytic leukemia (ALL), acute lyelogenous leukemia (AML), chronic lymphocytic leukemia (CLL), chronic myelogenous leukemia (CML), hairy cell leukemia), mature B cell neoplasms (small lymphocytic lymphoma, B cell prolymphocytic leukemia, lymphoplasmacytic lymphoma (such as Waldenström's macroglobulinemia), splenic marginal zone lymphoma, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma (NMZL), follicular lymphoma, mantle cell lymphoma, diffuse B cell lymphoma, mediastinal (thymic) large B cell lymphoma, intravascular large B cell lymphoma, primary effusion lymphoma and Burkitt lymphoma/leukemia), mature T cell and natural killer (NK) cell neoplasms (T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides (Sezary syndrome), primary cutaneous anaplastic large cell lymphoma, lymphomatoid papulosis, angioimmunoblastic T cell lymphoma, unspecified peripheral T cell lymphoma and anaplastic large cell lymphoma), Hodgkin lymphoma (nodular sclerosis, mixed celluarity, lymphocyte-rich, lymphocyte depleted or not depleted, nodular lymphocyte-predominant), myeloma (multiple myeloma, indolent myeloma, smoldering myeloma), chronic myeloproliferative disease (CMPD) (such as chronic myelogenous leukaemia, chronic neutrophilic leukaemia, chronic eosinophilic leukaemia, polycythaemia vera, chronic idiopathic myelofibrosis, essential thrombocythaemia and unclassifiable chronic myeloproliferative disease), myelodysplastic/myeloproliferative disease (such as chronic myelomonocytic leukaemia, atypical chronic myeloid leukemia, juvenile myelomonocytic leukaemia and unclassifiable myelodysplastic/myeloproliferative disease), myelodysplastic syndromes (MDS) (such as refractory anemia, refractory anemia with ringed sideroblasts, refractory cytopenia with multilineage dysplasia, refractory anemia with excess blasts, unclassifiable myelodysplastic syndrome and myelodysplastic syndrome associated with isolated del(5q) chromosome abnormality), immunodeficiency-associated lymphoproliferative disorders, histiocytic and dendritic cell neoplasms, mastocytosis (such as cutaneous mastocytosis, indolent systemic mastocytosis (ISM), systemic mastocytosis with associated clonal haematological non-mast-cell-lineage disease (SM-AHNMD), aggressive systemic mastocytosis (ASM), mast cell leukemia (MCL), mast cell sarcoma (MCS) and extrcutaneous mastocytoma), chondrosarcoma, Ewing sarcoma, fibrosarcoma, malignant giant cell tumor, myeloma bone disease, osteosarcoma, breast cancer (hormone dependent, hormone independent), gynecological cancers (cervical, endometrial, fallopian tube, gestational trophoblastic disease, ovarian, peritoneal, uterine, vaginal and vulvar), basal cell carcinoma (BCC), squamous cell carcinoma (SCC), malignant melanoma, dermatofibrosarcoma protuberans, Merkel cell carcinoma, Kaposi's sarcoma, astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, malignant mesothelioma (peritoneal mesothelioma, pericardial mesothelioma, pleural mesothelioma), gastro-enteropancreatic or gastroenteropancreatic neuroendocrine tumor (GEP-NET), carcinoid, pancreatic endocrine tumor (PET), colorectal adenocarcinoma, colorectal carcinoma, aggressive neuroendocrine tumor, leiomyosarcomamucinous adenocarcinoma, Signet Ring cell adenocarcinoma, hepatocellular carcinoma, cholangiocarcinoma, hepatoblastoma, hemangioma, hepatic adenoma, focal nodular hyperplasia (nodular regenerative hyperplasia, hamartoma), non-small cell lung carcinoma (NSCLC) (squamous cell lung carcinoma, adenocarcinoma, large cell lung carcinoma), small cell lung carcinoma, thyroid carcinoma, prostate cancer (hormone refractory, androgen independent, androgen dependent, hormone-insensitive), and soft tissue sarcomas (fibrosarcoma, malignant fibrous hystiocytoma, dermatofibrosarcoma, liposarcoma, rhabdomyosarcoma leiomyosarcoma, hemangiosarcoma, synovial sarcoma, malignant peripheral nerve sheath tumor/neurofibrosarcoma, extraskeletal osteosarcoma).

An "autoimmune disease" as used herein is a disease or disorder arising from and directed against an individual's own tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitus); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; antiglomerular basement membrane disease; antiphospholipid syndrome; allergic neuritis; Graves' disease; Lambert-Eaton myasthenic syndrome; pemphigoid bullous; pemphigus; autoinimune polyendocrinopathies; Reiter's disease; stiffman syndrome; Beheet disease; giant cell arteritis; immune complex nephritis; IgA nephropathy; IgM polyneuropathies; immune thrombocytopenic purpura (ITP) or autoimmune thrombocytopenia.

In certain embodiments the cancer is a hematological cancer selected from mantle cell lymphoma, diffuse large B-cell lymphoma (DLBCL), T-cell lymphomas or leukemias (e.g., cutaneous T-cell lymphoma (CTCL), noncutaneous peripheral T-cell lymphoma, lymphoma associated with human T-cell lymphotrophic virus (HTLV), and adult T-cell leukemia/lymphoma (ATLL)), acute lymphocytic leukemia, acute myelogenous leukemia (e.g., acute monocytic leukemia and acute promyelocytic leukemia), chronic lymphocytic leukemia (e.g., chronic B cell leukemia), chronic myelogenous leukemia, Hodgkin's disease, non-Hodgkin's lymphoma (e.g., Burkitt's lymphoma), myeloma, multiple myeloma, and myelodysplastic syndrome. In certain embodiments, the cancer is selected from multiple myeloma and lymphoma.

In certain embodiments the cancer is a solid tumor, neuroblastoma, or melanoma selected from mesothelioma, brain neuroblastoma, retinoblastoma, glioma, Wilms' tumor, bone cancer and soft-tissue sarcomas, head and neck cancers (e.g., oral, laryngeal and esophageal), genitourinary cancers (e.g., prostate, bladder, renal, uterine, ovarian, testicular, rectal and colon), lung cancer (e.g., small cell carcinoma and non-small cell lung carcinoma, including squamous cell carcinoma and adenocarcinoma), breast cancer, pancreatic cancer, basal cell carcinoma, metastatic skin carcinoma, squamous cell carcinoma (both ulcerating and papillary type), stomach cancer, brain cancer, liver cancer, adrenal cancer, kidney cancer, thyroid cancer, medullary carcinoma, osteosarcoma, soft-tissue sarcoma, Ewing's sarcoma, reticulum cell sarcoma, and Kaposi's sarcoma. In certain embodiments, the cancer is selected from ovarian cancer (e.g., ovarian adenocarcinoma), non-small cell lung cancer, and colorectal cancer.

Also included are pediatric forms of any of the cancers described herein. This invention also provides a method for the treatment of drug resistant tumors. In certain embodiments, the drug resistant tumor is multiple myeloma.

With the term "drug resistant" is meant a condition which demonstrates intrinsic resistance or acquired resistance. With "intrinsic resistance" is meant the characteristic expression profile in cancer cells of key genes in relevant pathways, including but not limited to apoptosis, cell progression and DNA repair, which contributes to the more rapid growth ability of cancerous cells when compared to their normal counterparts. With "acquired resistance" is meant a multifactorial phenomenon occurring in tumor formation and progression that can influence the sensitivity of cancer cells to a drug. Acquired resistance may be due to several mechanisms such as but not limited to; alterations in drug-targets, decreased drug accumulation, alteration of intracellular drug distribution, reduced drug-target interaction, increased detoxification response, cell-cycle deregulation, increased damaged-DNA repair, and reduced apoptotic response. Several of said mechanisms can occur simultaneously and/or may interact with each other. Their activation and/or inactivation can be due to genetic or epigenetic events or to the presence of oncoviral proteins. Acquired resistance can occur to individual drugs but can also occur more broadly to many different drugs with different chemical structures and different mechanisms of action. This form of resistance is called multidrug resistance.

Another aspect of the invention relates to the use of one or more chemotherapeutic agents and proteasome inhibitor compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Alzheimer's disease, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

EXEMPLIFICATION

Example 1

Immunocompromised mice (BNX, Charles River Laboratories) were challenged with subcutaneous administration of RL human lymphoma cells ($1\times10^7$/mouse) on the right flank in a total volume of 0.1 mL phosphate buffered saline (PBS). When tumors were approximately 50 mm$^3$ in size (as indicated by the arrow in FIG. 1), mice were randomized to treatment groups (9 mice/group). Compound 1 was administered intravenously (IV) in a solution of 10% (w/v) sulfobutylether-betacyclodextrin in aqueous 10 mM citrate buffer pH 3.5. Administration was given on Days 1 and 2 each week. SAHA was formulated in 100% DMSO and administered intraperitoneally (IP) on Days 1-5 each week. ***=P<0.001 (Compound 1+SAHA vs. Vehicle) by two-way ANOVA and Bonferroni post-hoc comparisons.

Example 2

Cell Lines and Reagents: The human lymphoma (RL), non-small cell lung (A549) and colon (HT-29) tumor cell lines were purchased from ATCC (Manassas, Va.). The HDAC inhibitor vorinostat was purchased from Cayman Chemical (Ann Arbor, Mich.). Docetexel was purchased from Sigma Chemicals (Ann Arbor, Mich.). Doxil prescription was purchased from a local pharmacy.

Toxicity Studies: 4-6 weeks old female BNX mice were treated with chemotherapeutic agents of multiple classes as monotherapy or in combination with carfilzomib. Two weeks toxicity studies were performed at doses and dose schedules as mentioned in the figure legend. Toxicity was measured as body weight loss three times a week.

Xenograft studies: Tumors were established by subcutaneous (s.c.) injection of cell lines (passage number<9 and viability>95% at the time of implantation) in the right flank of BNX mice (n=8/9 per group). RL (0.1 mL) cell suspensions containing $1 \times 10^7$ cells. $5 \times 10^6$ cell suspension (0.1 mL) were injected in case of HT-29, ES2 and A549 cells. Mice were randomized into treatment groups and dosing initiated when tumors size was approximately 100 mm$^3$. In all treatment groups, tumors were measured three times weekly by recording the longest perpendicular diameters and tumor volumes were calculated using the equation V (mm$^3$)= (length×width$^2$)/2.

Statistical analysis: For comparisons of treatment groups, a two-way ANOVA followed by Bonferroni post hoc analysis using GraphPad Prism Software (version 4.01) was performed. Statistical significance was achieved when $p<0.05$.

Figure 2:
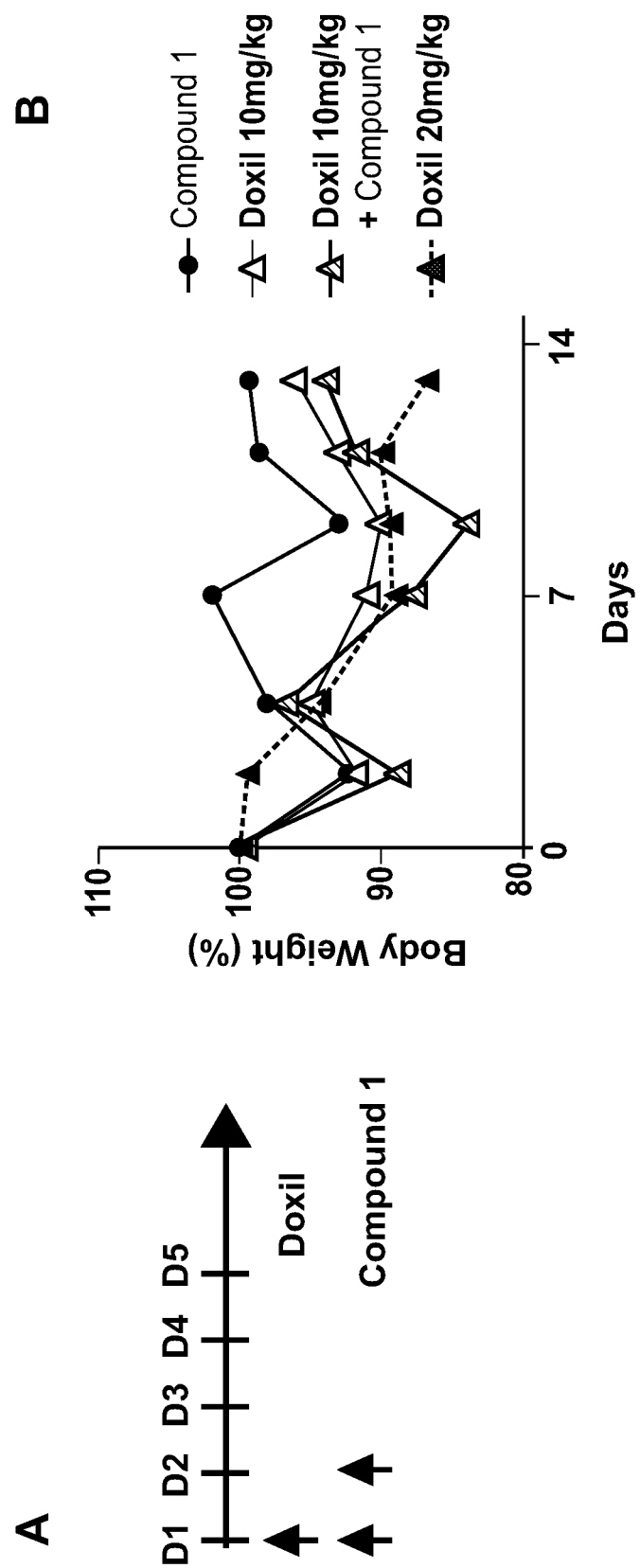
FIG. 2 shows: (A) the dosing schedule for combination therapy with Doxil and Compound 1, and (B) the toxicity study for combination therapy with Doxil and Compound 1, where Doxil is administered at 10 or 20 mg/kg and Compound 1 is administered at 5 mg/kg.

Compound 1 in combination with Doxil was well tolerated with clinically relevant dose schedule at MTD 10 mg/kg Doxil→Q7D(iv) and MTD 5 mg/kg carfilzomib→QD×2(iv). The dose schedule as shown in FIG. 2A was Doxil day 1 (iv), after one hour Compound 1 day 1, 2 (iv). A two weeks toxicity study was performed in BNX mice and body weight loss was assessed (n=5) as shown in FIG. 2B where the maximum tolerated dose (MTD) of Doxil as single agent in BNX mice was 20 mg/kg while the MTD of Doxil in combination with Compound 1 (5 mg/kg) at tested dose schedule was 10 mg/kg.

| % Body weight loss | | | |
|---|---|---|---|
| Doxil (iv) (2 weeks) | | | |
| Combination | Dose | Schedule | Weight loss (%) |
| None | 10 mg/kg | Q7D | 10 |
| Compound 1 (5 mg/kg) | 10 mg/kg | Q7D | 16 |
| None | 20 mg/kg | Q7D | 15 |

Figure 3:
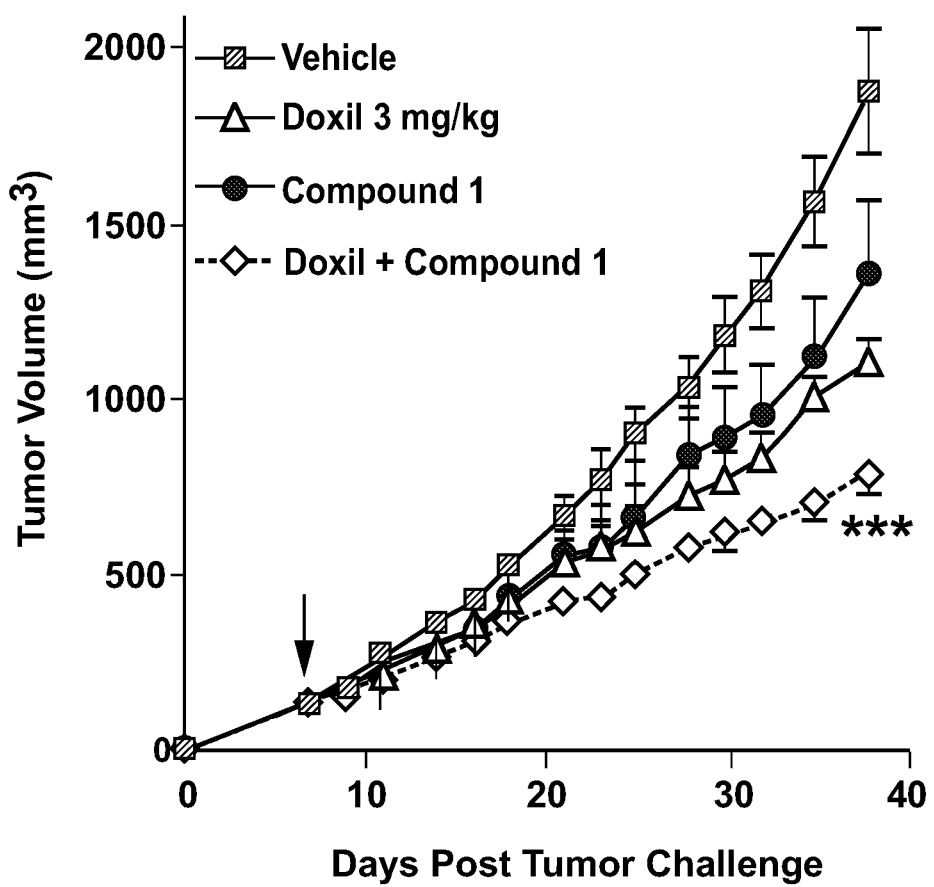
FIG. 3 shows colorectal HT29 tumor size over time for treatment with vehicle, Doxil (3 mg/kg), Compound 1 (5 mg/kg), and a combination of Compound 1 and Doxil.
Figure 4:
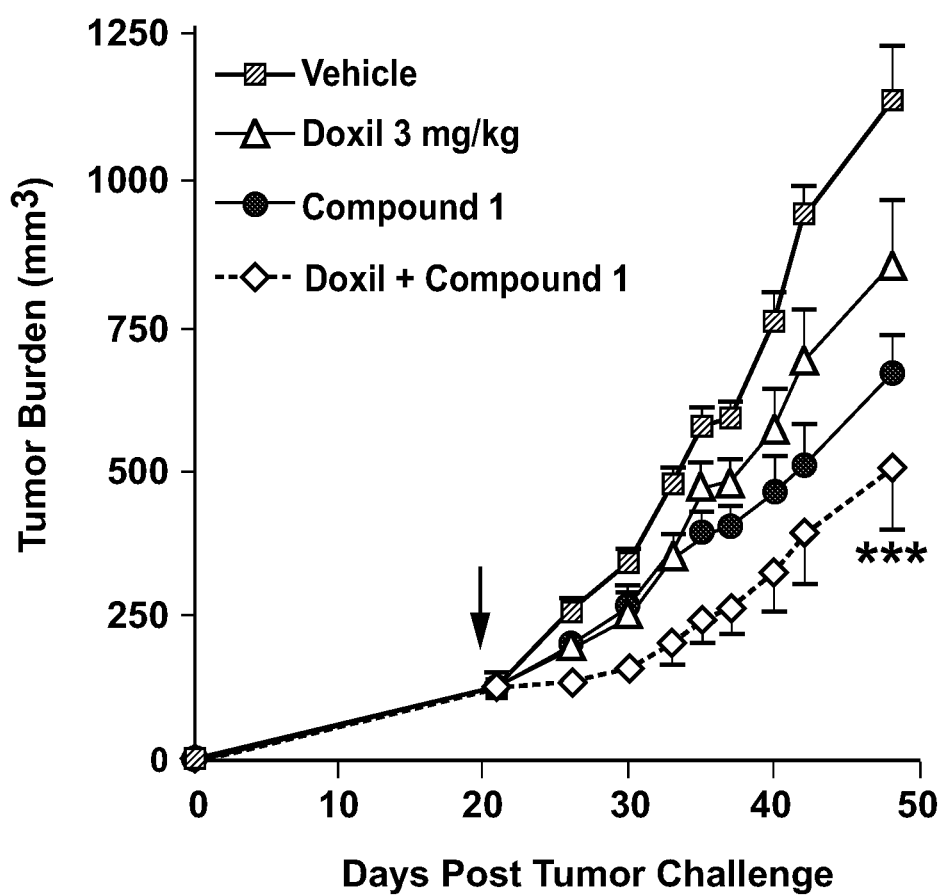
FIG. 4 shows non-small cell lung A549 tumor size over time for treatment with vehicle, Doxil (3 mg/kg), Compound 1 (5 mg/kg), and a combination of Compound 1 and Doxil.

Compound 1 at MTD (5 mg/kg) and sub-MTD of Doxil (3 mg/kg) (n=10/group) on established HT29 colorectal xenograft model shows increased anti-tumor activity, (Combination treatment *p<0.001 vs. control or caifilzomib alone; p<0.01 vs. Doxil alone) as shown in FIG. 3 (arrow indicates start of dosing period). Similar observations were noted on established A549 non-small cell lung cancer xenograft model. (Combination treatment *p<0.001 vs. control or Doxil alone; No significance vs. carfilzomib alone) as shown in FIG. 4** (arrow indicates start of dosing period).

Figure 5:
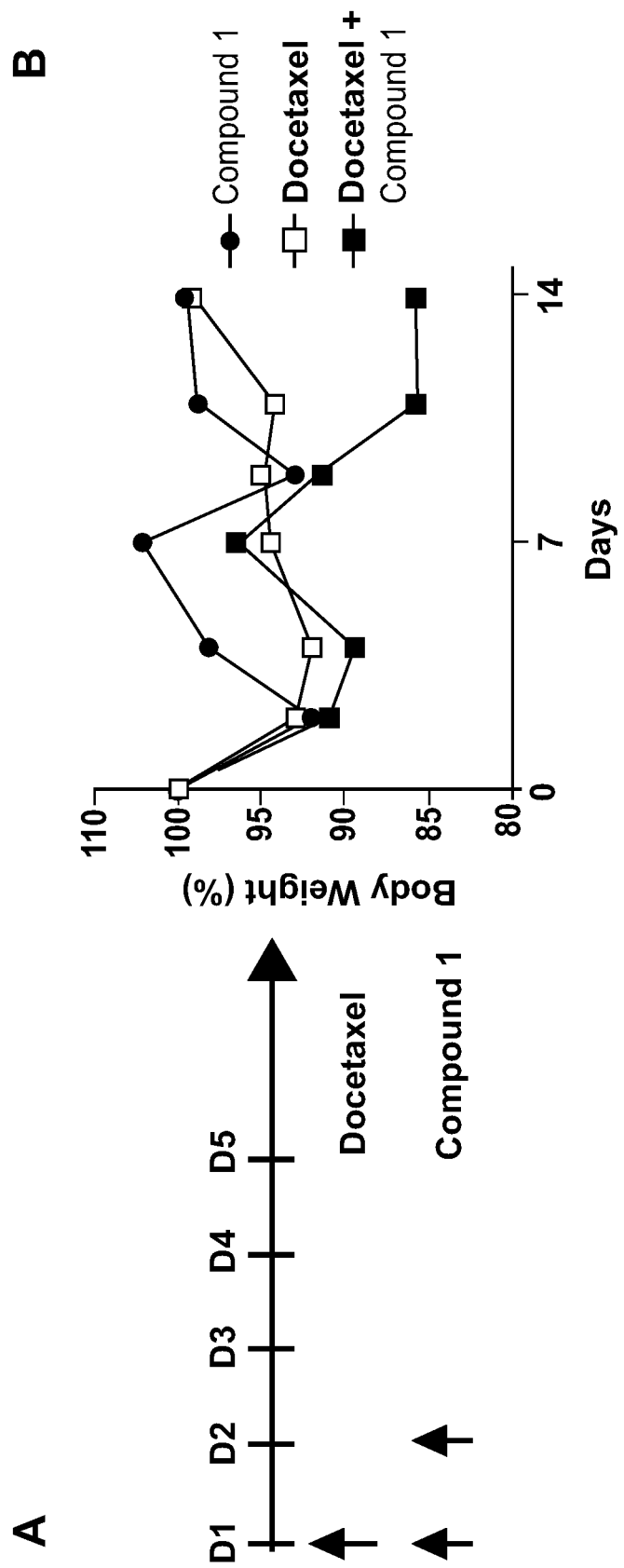
FIG. 5 shows: (A) the dosing schedule for combination therapy with docetaxel and Compound 1, and (B) the toxicity study for combination therapy with docetaxel and Compound 1, wherein docetaxel is administered at 10 mg/kg and Compound 1 is administered at 5 mg/kg.

Compound 1 in combination with docetaxel was well tolerated with clinically relevant dose schedule at MTD 10 mg/kg docetaxel→Q7D (iv) and MTD 5 mg/kg of Compound 1→QD×2(iv). The dose schedule as shown in FIG. 5A was docetaxel day 1 (iv), after one hour Compound 1 day 1, 2 (iv). A two weeks toxicity study was then performed in BNX mice and body weight loss was assessed (n=5) where the MTD of docetaxel in combination with carfilzomib at this dose schedule was 10 mg/kg.

| % Body weight loss | | | |
|---|---|---|---|
| Docetaxel (iv) (2 weeks) | | | |
| Combination | Dose | Schedule | Weight loss (%) |
| None | 10 mg/kg | Q7D | None |
| Compound 1 | 10 mg/kg | Q7D | 16 |

Figure 6:
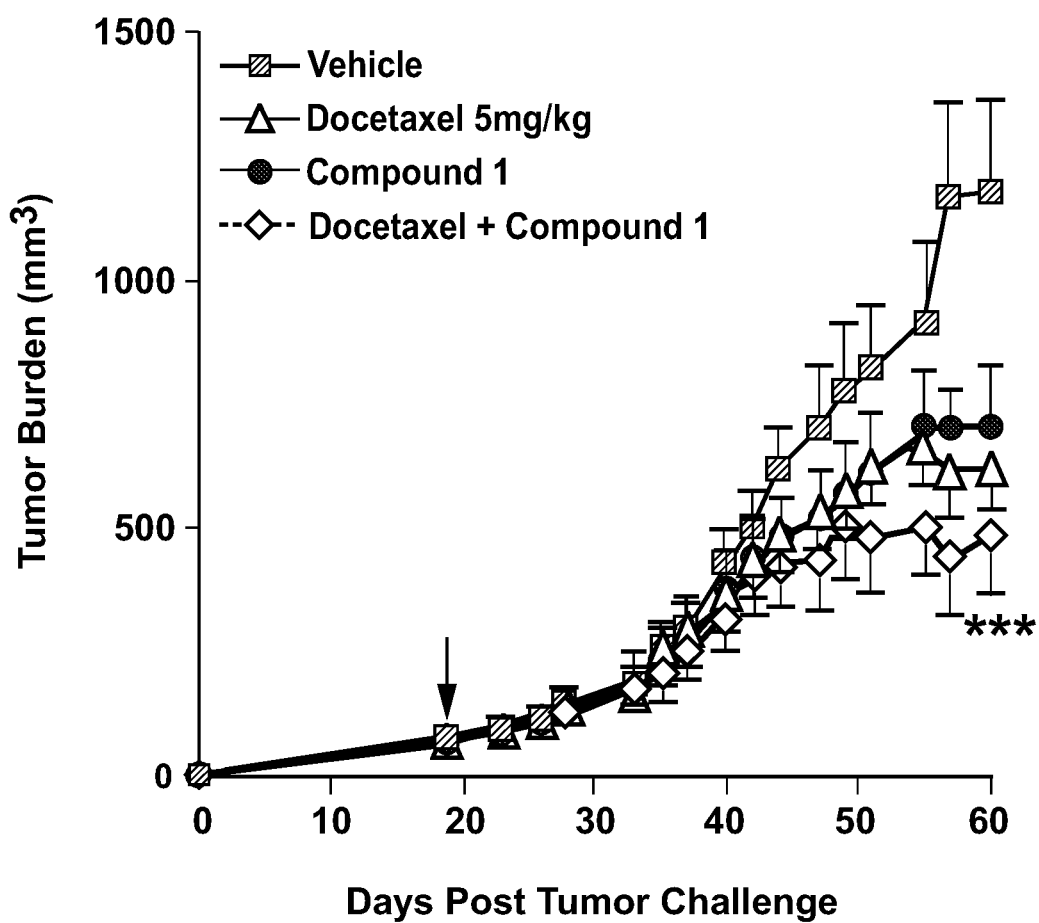
FIG. 6 shows non-small cell lung A549 tumor size over times for treatment with vehicle, Compound 1 (5 mg/kg), docetaxel (5 mg/kg), and a combination of Compound 1 and docetaxel.
Figure 7:
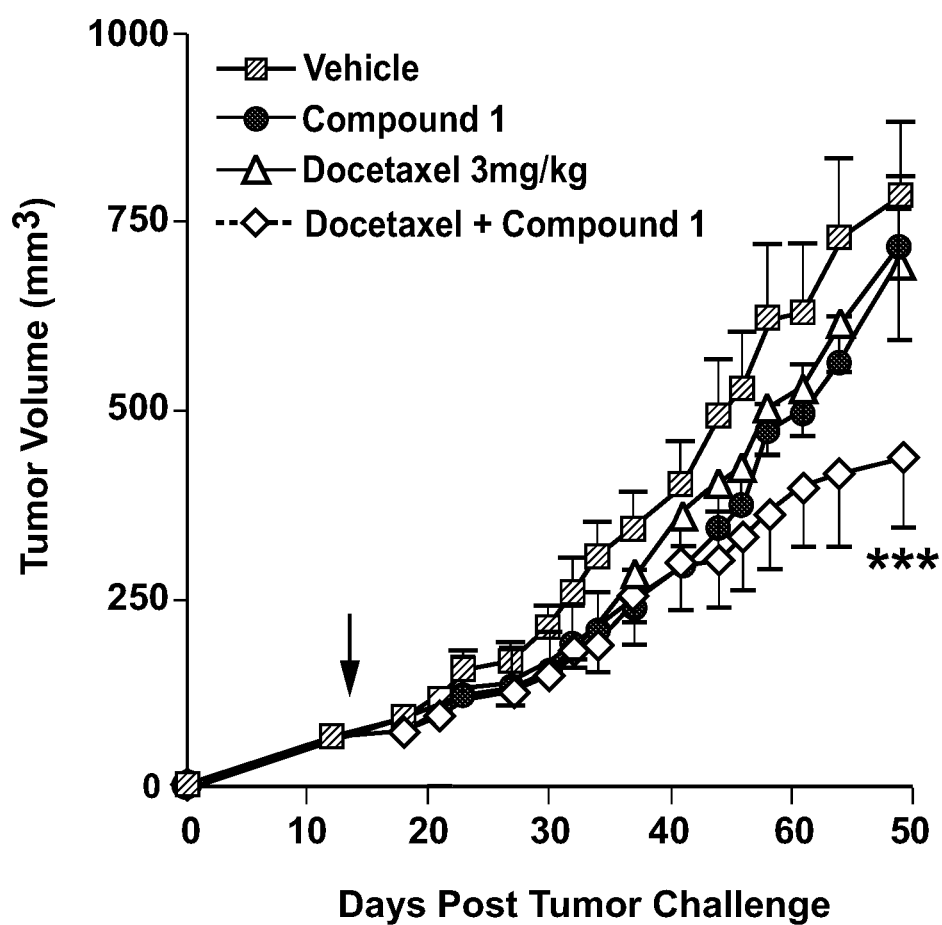
FIG. 7 shows non-small cell lung A549 tumor size over time for treatment with vehicle, Compound 1 (3 mg/kg), docetaxel (3 mg/kg), and a combination of Compound 1 and docetaxel.

A combination of Compound 1 at MTD (5 mg/kg) and sub-MTD of docetaxel (5 mg/kg) (n=10/group) on established A549 non-small cell lung cancer xenograft model, (Combination treatment *p<0.001 vs. control; p<0.05 vs. carfilzomib alone, NS vs docetaxel) as shown in FIG. 6 (arrow indicates start of dosing period). A combination of Compound 1 at sub-MTD (3 mg/kg) and sub-MTD of docetaxel (5 mg/kg) (n=10/group) on established A549 non-small cell lung cancer xenograft model, (Combination treatment *p<0.001 vs. control; p<0.01 vs. carfilzomib and docetaxel) is shown in FIG. 7 (arrow indicates start of dosing period).

Figure 8:
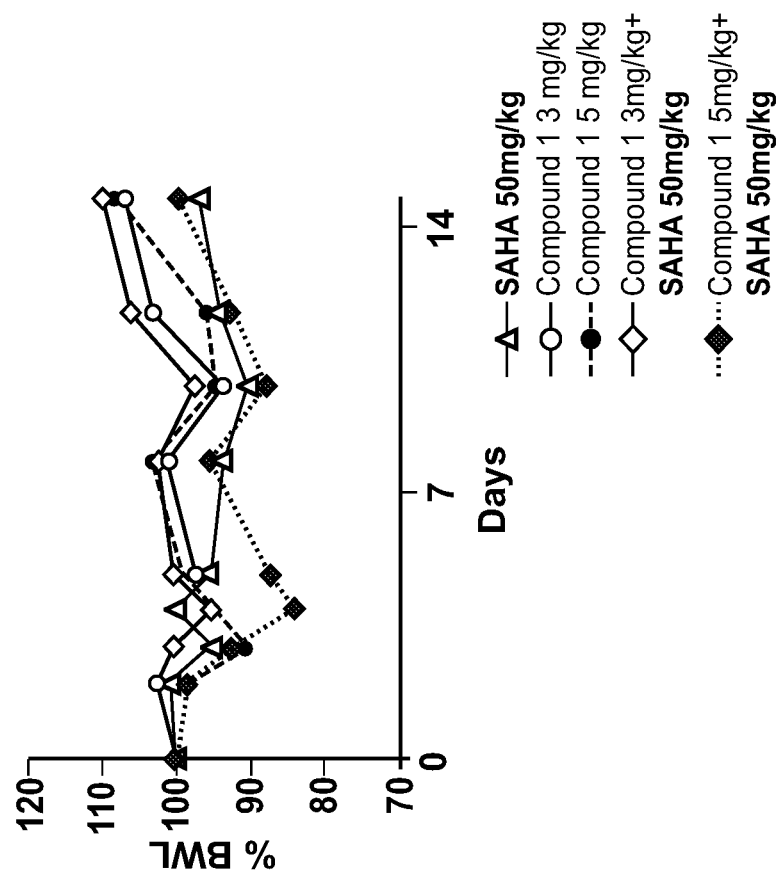
FIG. 8 shows: (A) the dosing schedule for combination therapy with SAHA and Compound 1, and (B) the toxicity study for combination therapy with vorinostat and Compound 1, wherein SAHA is administered at 50 mg/kg and Compound 1 is administered at 3 or 5 mg/kg.
Figure 8:
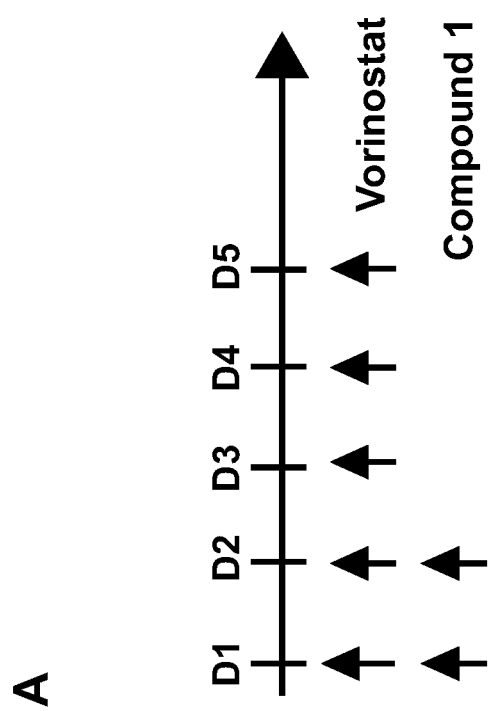

A combination of Compound 1 and vorinistat was well tolerated with clinically relevant dose schedule at 50 mg/kg→QD×5 vorinostat (ip) and MTD 5 mg/kg Compound 1→QD×2(iv). The MTD of vorinostat was not determined. Vorinostat was administered day 1-5 (ip), after one hour Compound 1 day 1, 2 (iv) as shown in FIG. 8A. Compound 1 and vorinostat treatment in BNX mice toxicity, as measured by body weight loss (BWL), was similar amongst the treatment groups suggesting that the combination was well tolerated in experimental animals (FIG. 8B).

Figure 9:
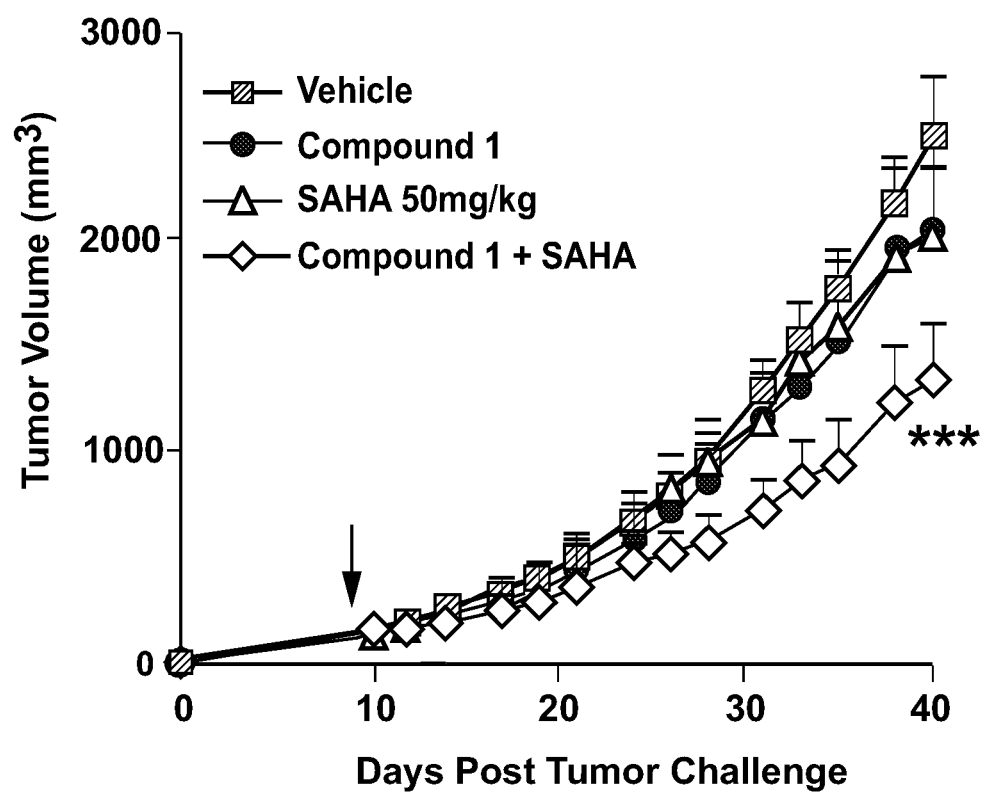
FIG. 9 shows lymphoma RL tumor size over time for treatment with vehicle, Compound 1 (3 mg/kg), SAHA (50 mg/kg), and a combination of Compound 1 and SAHA.
Figure 10:
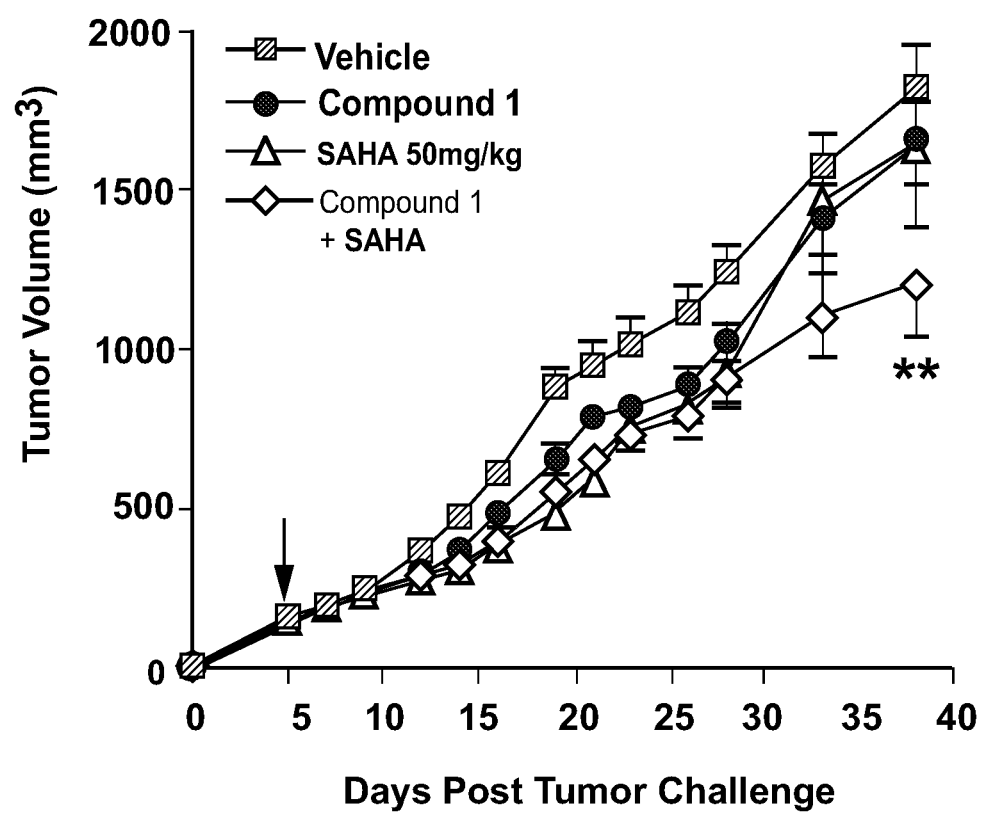
FIG. 10 shows ovarian ES2 tumor size over time for treatment with vehicle, Compound 1 (5 mg/kg), SAHA (50 mg/kg), and a combination of Compound 1 and SAHA.

The effect of the combination of Compound 1 (3 mg/kg) and vorinostat (50 mg/kg) (n=8/group) on established RL tumors is shown in FIG. 9 (arrow indicates start of dosing period). The effect of the combination of Compound 1 (3 mg/kg) and vorinostat (50 mg/kg) (n=8/group) on established ES2 tumors. , P<0.01; and *, P<0.001 vs monotherapy and vehicle is shown in FIG. 10 (arrow indicates start of dosing period).

Compound 1 treatment was well tolerated in combination with a histone deacytelase inhibitor (vorinostat), a microtubule disrupting agent (docetaxel) and an anthracycline (Doxil) at clinically relevant dose schedules for each individual agent. The combination of Compound 1 and vorinostat resulted in a significant reduction in lymphoma (RL) tumor growth compared to vehicle controls or treatment with either single agent (p<0.001 vs. control; p<0.01 vs. Compound 1 or vorinostat alone). The combination of Compound 1 and docetaxel resulted in a significant reduction in A549 tumor growth compared to vehicle controls or treatment with either single agent (p<0.001 vs. control; p<0.01 vs. carfilzomib or docetaxel alone). Similar observations were noted in the HT-29 xenograft model where a Compound 1 and Doxil combination significantly reduced tumor burden (p<0.001 vs. control or carfilzomib alone; p<0.01 vs. Doxil alone). Compound 1 and Doxil at sub-MTD doses shows a synergistic anti-tumor effect in solid tumor model. Similarly, Compound 1 in combination with docetaxel at sub-MTD doses induced a synergistic anti-tumor effect in human lung cancer model. Compound 1 in combination with vorinostat induced a synergistic anti-tumor effect in lymphoma model. Compound 1 in combination with vorinostat indicated an effective anti-tumor property in ovarian cancer model.

Example 3

Compound 1 was tested at 6.58 nM in combination with melphalan at four different doses: 11.1, 7.4, 4.9 and 3.3 μM.

Figure 11:
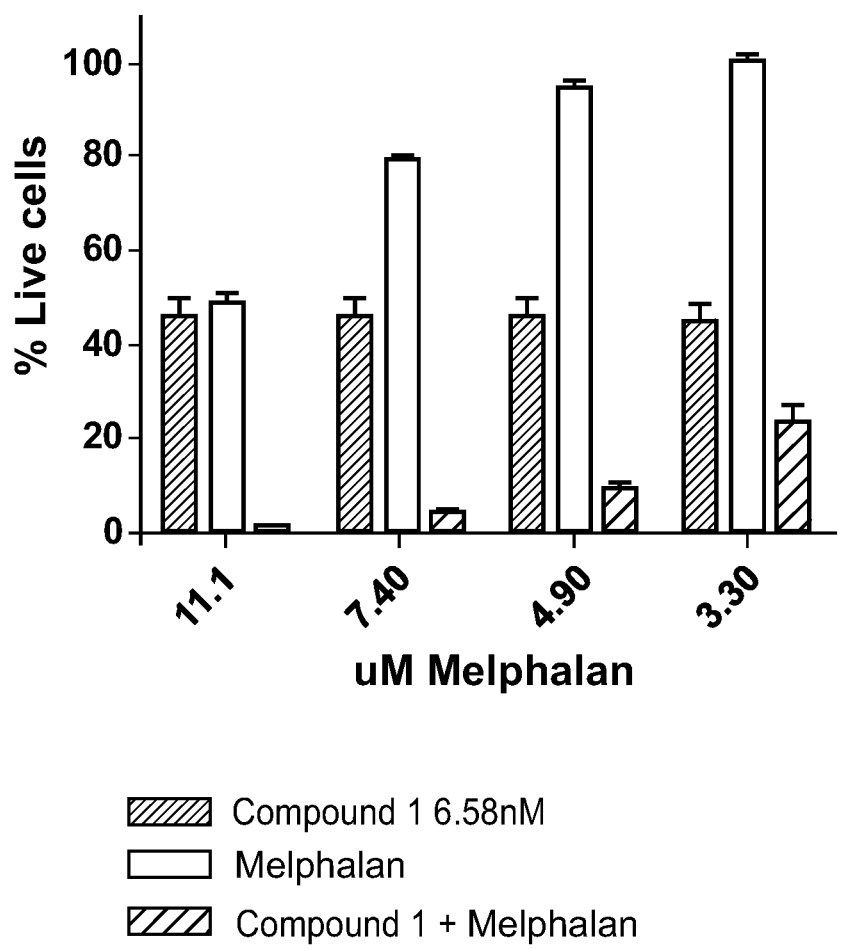
FIG. 11 shows the effect of a combination of Compound 1 and melphalan on MM1.S cells.
Figure 12:
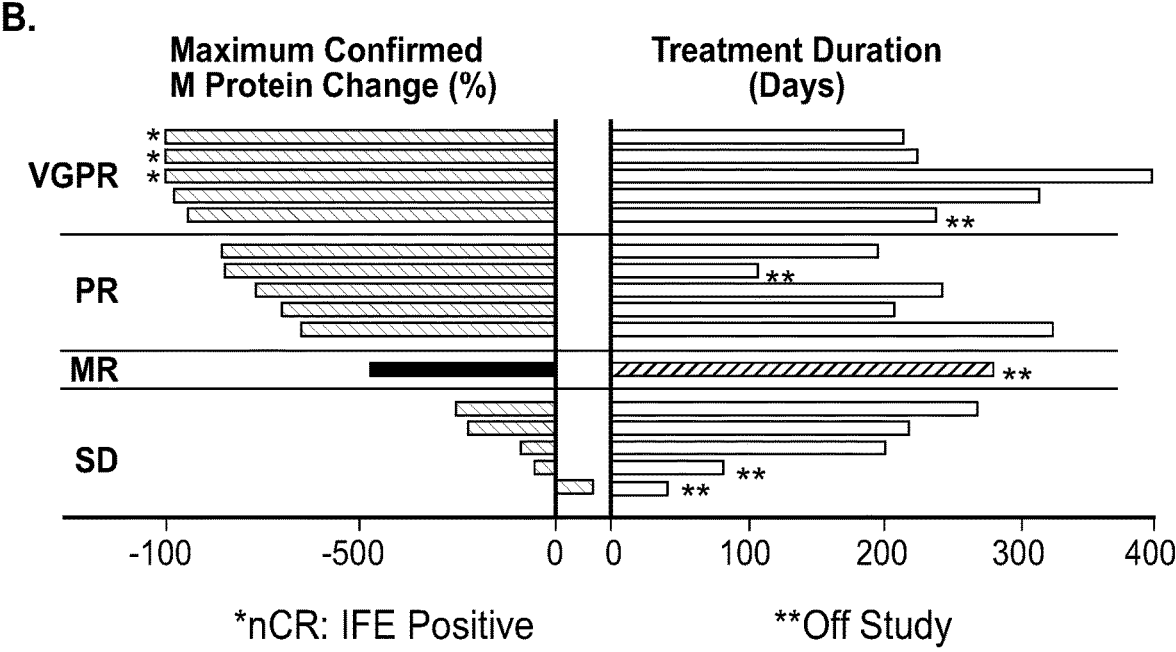
FIG. 12 shows: (A) preliminary results of a phase Ib dose escalation study of carfilzomib plus lenalidomide and low-dose dexamethasone in relapsed multiple myeloma patients. Within the first three cohorts, seventeen patients were evaluable for response and toxicity. The maximum tolerated dose (MTD) was not yet reached and not drug-related grade 3 or 4 serious adverse events were reported; and (B) preliminary results of a phase Ib dose escalation study of carfilzomib plus lenalidomide and low-dose dexamethasone in relapsed multiple myeloma patients. Responses were durable.

MM1.S (multiply myeloma, dexamethasone sensitive) cells were plated at 200,000 cells/mL in 45 μL then pretreated with melphalan for 24 hours. Compound 1 was then added and the cells were incubated for an additional 24 hours at 6.58 nM. A 1:1 ratio of Cell titer glo solution was then added to the cell samples and read for viability. Combination index values were calculated using the Calcusyn program where values<0.9=synergy, 0.9-1.0=additive and >1.1=antagonistic. Results indicate that Compound 1 and melphalan show synergistic and additive effects at these concentrations as shown in FIG. 11.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A method of treating multiple myeloma in a patient, the method comprising administering to the patient in need of treatment a combination of: (a) melphalan, and (b) an effective amount of an epoxy ketone proteasome inhibitor having the structure of

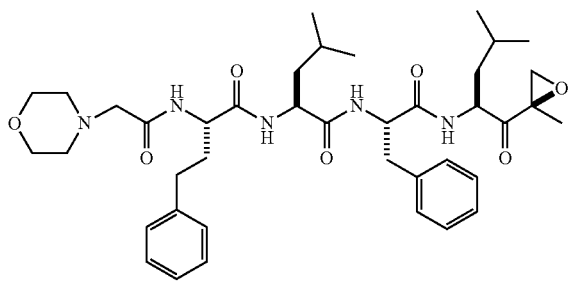 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

or a pharmaceutically acceptable salt thereof.

2. The method of claim 1, wherein the peptide epoxy ketone proteasome inhibitor and the melphalan are administered simultaneously.

3. The method of claim 1, wherein the melphalan is administered within 5 minutes to within 48 hours prior to or after administration of the peptide epoxy ketone proteasome inhibitor.

4. The method of claim 1, wherein the melphalan is administered within 5 minutes to within 1 hour prior to or after administration of the peptide epoxy ketone proteasome inhibitor.

5. The method of claim 1 wherein the peptide epoxy ketone proteasome inhibitor is administered in a dose of at least 15 mg/m$^2$.

6. A method of treating multiple myeloma in a patient, the method consisting essentially of administering to the patient in need of treatment a combination of: (a) melphalan, and (b) an effective amount of an epoxy ketone proteasome inhibitor having the structure of

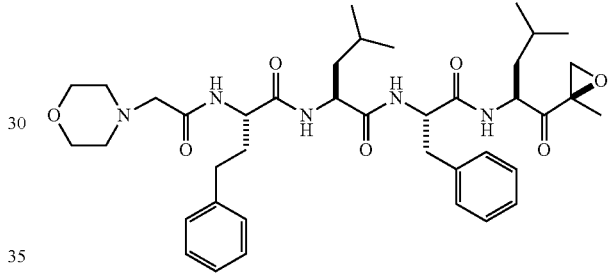

or a pharmaceutically acceptable salt thereof.

* * * * *